(12) United States Patent
Kariniemi et al.

(10) Patent No.: US 8,821,529 B2
(45) Date of Patent: Sep. 2, 2014

(54) DEVICE AND METHOD FOR OCCLUDING A SEPTAL DEFECT

(75) Inventors: Ryan Douglas Kariniemi, Cokato, MN (US); Mathias C. Glimsdale, St. Michael, MN (US); John Oslund, Blaine, MN (US); Derek Randall Wise, New Brighton, MN (US)

(73) Assignee: AGA Medical Corporation, Plymouth, MN (US)

( * ) Notice: Subject to any disclaimer, the term of this patent is extended or adjusted under 35 U.S.C. 154(b) by 416 days.

(21) Appl. No.: 13/072,337

(22) Filed: Mar. 25, 2011

(65) Prior Publication Data

US 2012/0245623 A1   Sep. 27, 2012

(51) Int. Cl.
    *A61B 17/00*   (2006.01)

(52) U.S. Cl.
    USPC ........... 606/200; 606/151; 606/153; 606/213; 606/216; 606/157; 606/158; 606/194; 623/1.1; 623/1.11; 623/1.23; 623/1.25

(58) Field of Classification Search
    USPC ......... 606/151, 157, 158, 200, 213, 216, 191, 606/194, 195, 198; 623/1.1, 1.11, 1.25, 623/1.51
    See application file for complete search history.

(56) References Cited

U.S. PATENT DOCUMENTS

| | | |
|---|---|---|
| 4,991,602 A | 2/1991 | Amplatz et al. |
| 5,067,489 A | 11/1991 | Lind |
| 5,108,420 A | 4/1992 | Marks |
| 5,725,552 A | 3/1998 | Kotula et al. |
| 5,846,261 A | 12/1998 | Kotula et al. |
| 5,944,738 A | 8/1999 | Amplatz et al. |
| 5,976,174 A | 11/1999 | Ruiz |
| 6,077,291 A | 6/2000 | Das |
| 6,123,715 A | 9/2000 | Amplatz |
| 6,214,029 B1 | 4/2001 | Thill et al. |
| 6,334,864 B1 | 1/2002 | Amplatz et al. |
| 6,368,339 B1 | 4/2002 | Amplatz |
| 6,402,772 B1 | 6/2002 | Amplatz et al. |
| 6,447,531 B1 | 9/2002 | Amplatz |
| 6,551,344 B2 | 4/2003 | Thill |
| 6,579,303 B2 | 6/2003 | Amplatz |
| 6,911,037 B2 | 6/2005 | Gainor et al. |

(Continued)

OTHER PUBLICATIONS

International Search Report and Written Opinion from International Patent Application No. PCT/US2012/028271, mailed Jul. 18, 2012.

(Continued)

*Primary Examiner* — Vy Q Bui
(74) *Attorney, Agent, or Firm* — Armstrong Teasdale LLP

(57) ABSTRACT

A device for occluding a septal defect is provided. In general, the occluding device has a contracted state that allows the occluding device to be received within a delivery device for deployment to the site of the defect and an expanded state that is achieved when the occluding device is deployed from the delivery device. The occluding device has a proximal portion, which may be substantially circular, a distal portion, which may be substantially ovaloid, and a connecting portion extending between the two. The distal portion may define first and second outer parts at opposite ends of the major axis, which may be bent or curved. The configuration of the proximal and distal portions allow the occluding device to securely engage the septal wall and be kept in position at the septal defect without causing substantial interference with the functioning of adjacent heart structures.

41 Claims, 16 Drawing Sheets

(56) References Cited

U.S. PATENT DOCUMENTS

| | | |
|---|---|---|
| 7,041,125 B2 | 5/2006 | Hwang et al. |
| 7,144,410 B2 | 12/2006 | Marino et al. |
| 7,288,105 B2 | 10/2007 | Oman et al. |
| 8,313,505 B2 * | 11/2012 | Amplatz et al. ............ 606/200 |
| 2001/0003801 A1 | 6/2001 | Strecker |
| 2002/0198563 A1 | 12/2002 | Gainor et al. |
| 2003/0055455 A1 | 3/2003 | Yang et al. |
| 2003/0139819 A1 | 7/2003 | Beer et al. |
| 2004/0236403 A1 | 11/2004 | Leonhardt et al. |
| 2005/0228434 A1 | 10/2005 | Amplatz et al. |
| 2005/0267523 A1 | 12/2005 | Devellian et al. |
| 2006/0122647 A1 | 6/2006 | Callaghan et al. |
| 2006/0241690 A1 | 10/2006 | Amplatz et al. |
| 2007/0066993 A1 | 3/2007 | Kreidler |
| 2007/0118207 A1 | 5/2007 | Amplatz et al. |
| 2007/0123927 A1 | 5/2007 | Farnan |
| 2007/0233171 A1 | 10/2007 | Gilson |
| 2007/0265656 A1 | 11/2007 | Amplatz et al. |
| 2008/0033475 A1 * | 2/2008 | Meng ............................ 606/191 |
| 2008/0200945 A1 | 8/2008 | Amplatz et al. |
| 2008/0215008 A1 | 9/2008 | Nance et al. |
| 2008/0221657 A1 | 9/2008 | Laroya et al. |
| 2008/0262518 A1 | 10/2008 | Freudenthal |
| 2009/0018562 A1 | 1/2009 | Amplatz et al. |
| 2009/0062841 A1 | 3/2009 | Amplatz et al. |
| 2009/0157162 A1 | 6/2009 | Chow et al. |
| 2009/0187214 A1 | 7/2009 | Amplatz et al. |
| 2009/0264980 A1 | 10/2009 | Mackay |
| 2010/0121370 A1 | 5/2010 | Kariniemi |

OTHER PUBLICATIONS

International Search Report and Written Opinion from International Patent Application No. PCT/US2012/028266, mailed Jul. 5, 2012.

* cited by examiner

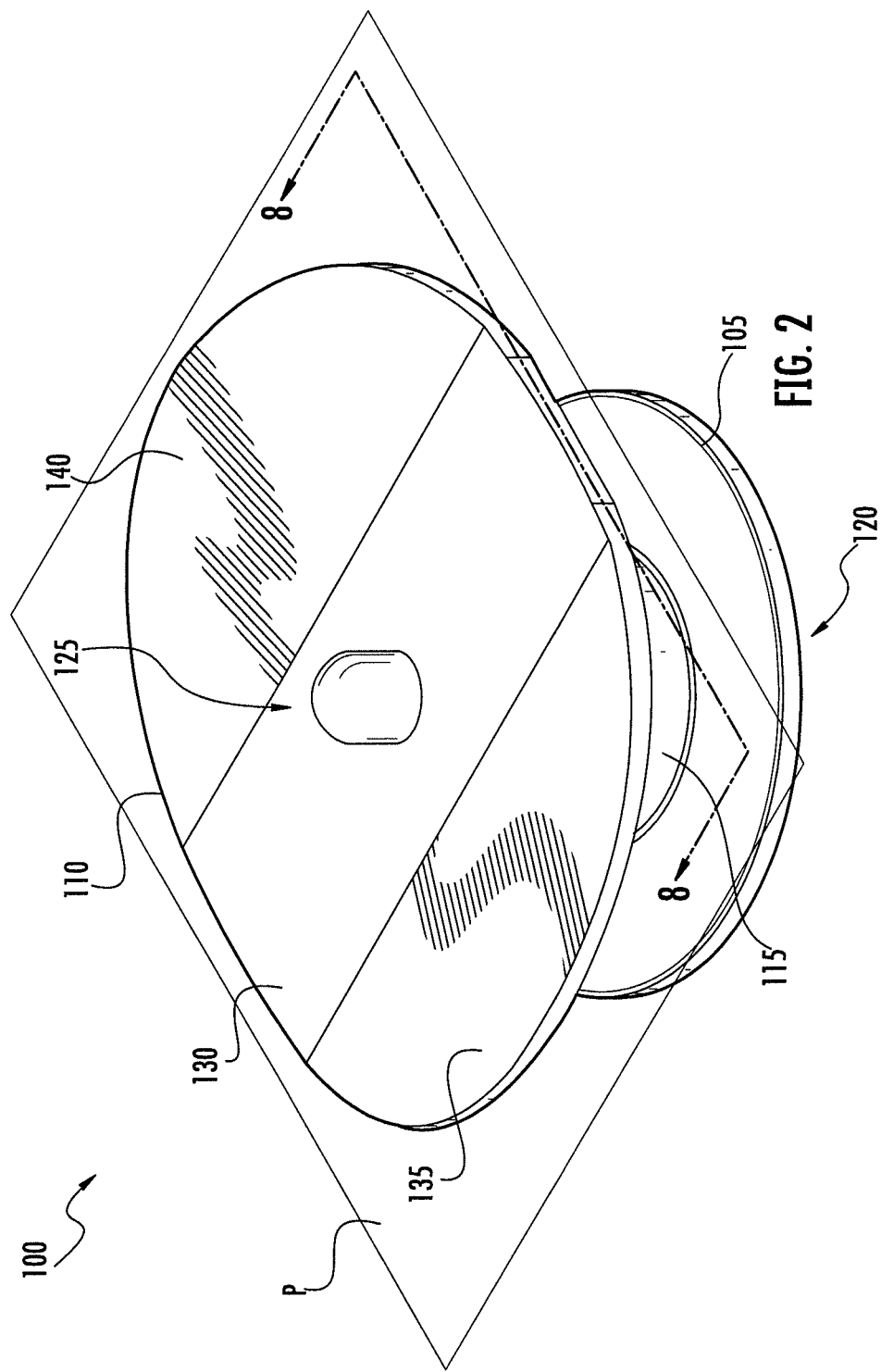

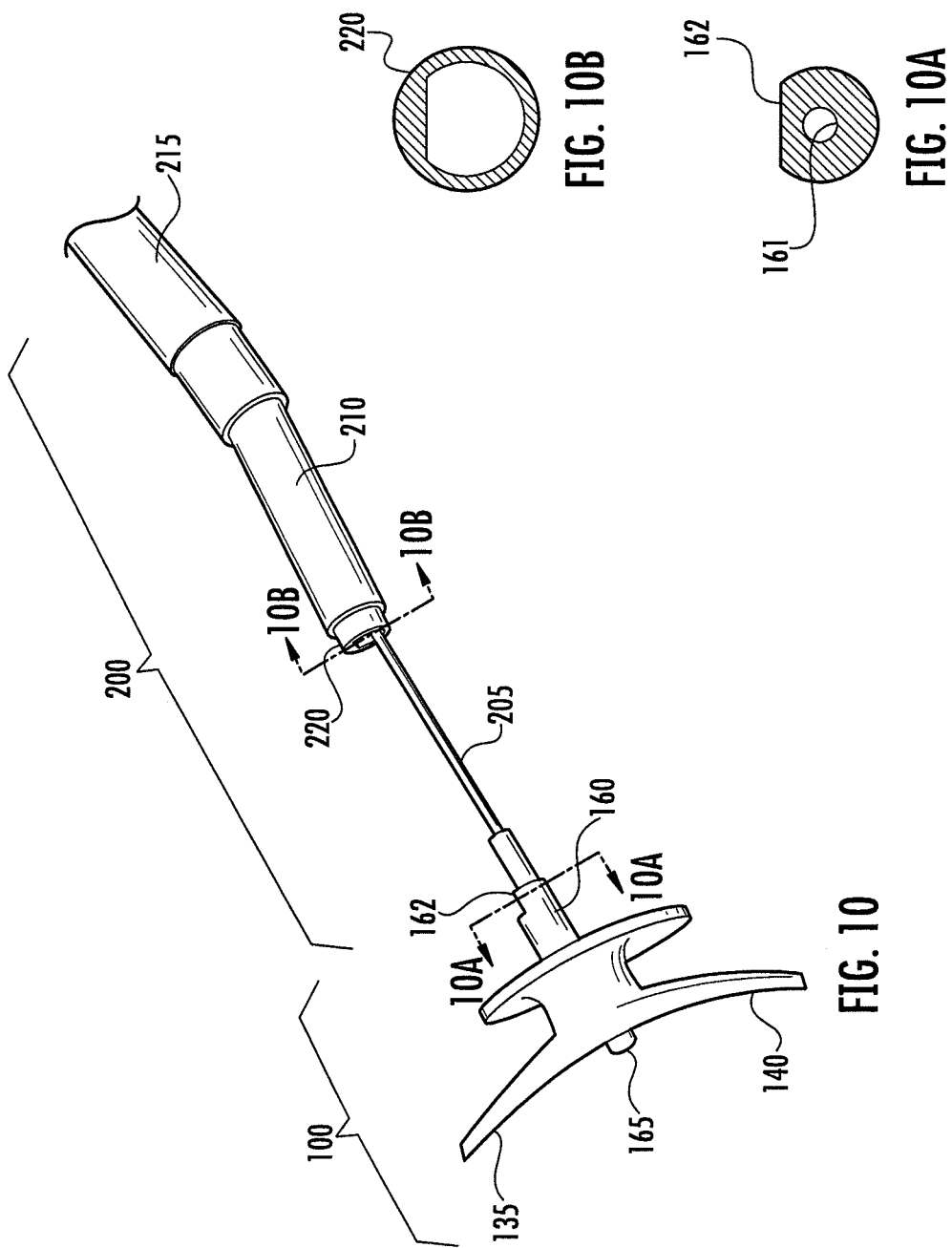

DEVICE AND METHOD FOR OCCLUDING A SEPTAL DEFECT

BACKGROUND

I. Field of the Invention

Embodiments of the present invention relate generally to intravascular devices for treating certain medical conditions. In particular, embodiments are directed to devices for occluding an abnormal opening in a patient's body, such as a septal defect.

II. Description of the Related Art

Over the past few decades, advances have been made in the diagnosis and treatment of septal defects, such as atrial septal defects and ventricular septal defects. In general, septal defects are congenital heart defects in which the inner wall separating the left and right sides of the heart (i.e., the septum) has a hole or an opening that has failed to close.

FIGS. 1A and 1B show schematic representations of a patient's heart 5. In FIG. 1A, the patient's heart 5 has a hole 10 in the septum 15 between the heart's two upper chambers (the left atrium 20 and the right atrium 25), called an atrial septal defect (ASD). In FIG. 1B, the patient's heart 5 has a hole 10 in the septum 15 between the heart's two lower chambers (the left ventricle 30 and the right ventricle 35), called a ventricular septal defect (VSD). Ventricular septal defects can occur in any location of the ventricular septum. Two common locations for these defects are the perimembranous septum and the muscular septum.

As a result of an atrial septal defect or a ventricular septal defect, blood is able to pass from the left side of the heart to the right side, mixing oxygen-rich blood with oxygen-poor blood. This can cause a variety of problems for the individual as time goes on, such as pulmonary hypertension, right-sided heart failure, atrial fibrillation or flutter, and stroke.

One way to non-surgically treat septal defects is to permanently place an occluding device in the heart to cover the hole. The occluding device is typically delivered to the site of the septal defect using a catheter, which is inserted into the blood vessel in the patient's groin and passed through vessels into the heart's chambers. At the site of the defect, the occluding device may be deployed from the catheter and permanently placed in the hole. With time, the lining of the heart wall should grow over the device to seal the hole completely.

The configuration of the particular occluding device used to repair the defect may depend on the size and location of the defect. For example, the force needed to retain the device within the defect typically increases as the size of the defect increases. In addition, the location of the septal defect with respect to adjacent heart structures may also be taken into consideration. For example, in a membranous type ventricular septal defect, it may be difficult to effectively position a prior art occluding device without at least partially interfering with the functioning of valves such as the aortic valve 40 and/or the tricuspid valve 41 (shown in FIGS. 1A and 1B), causing valve regurgitation or some other valve malfunction.

Accordingly, there is a need for an improved occluding device that is easily delivered to the defect site, can be accurately placed at the defect site, resists dislodgement, conforms to the patient's anatomy, does not interfere with adjacent heart structures or heart conduction pathways, and overcomes the shortcomings of conventional solutions.

SUMMARY OF THE INVENTION

Embodiments therefore provide a device for occluding a septal defect. In general, the occluding device is configured to conform to the anatomy of the target site and to be atraumatic to the surrounding tissues, structures, or functions. The device described herein may have a contracted state (e.g., when the device is received within a delivery device, such as a catheter, for deployment to the site of the defect) and an expanded state (e.g., when the device is deployed from the delivery device). In the expanded state, embodiments of the occluding device include a proximal portion that is substantially circular, a distal portion that is substantially ovaloid, and a connecting portion extending between the proximal and distal portions. The configuration of the proximal and distal portions are such that, when the occluding device is deployed and the connecting portion is disposed within the septal defect, each of the proximal portion and the distal portion engages a corresponding septal wall surface to maintain proper positioning of the occluding device with respect to the defect without interfering with the proper functioning of adjacent heart structures, such as the aortic valve.

In some embodiments, a device for occluding a septal defect is provided, wherein the device is configured to be constrained in a contracted state and to assume an expanded state when unconstrained. The occluding device may include a proximal portion, a distal portion, and a connecting portion extending between the proximal portion and the distal portion. In the expanded state, the distal portion may define a central part and first and second outer parts extending from the central part. The central part may define a plane, and each of the first and second outer parts may extend distally out of the plane. Moreover, the occluding device may be configured to be received within a delivery device in a contracted state and may be configured to self expand to the expanded state when deployed from the delivery device such that each of the proximal portion and the distal portion engages a corresponding septal wall surface and the connecting portion is disposed within the septal wall. In the expanded state, the central part of the distal portion may be substantially flat.

In some embodiments, in the expanded state, the proximal portion may be substantially circular when viewed from a proximal end of the device, and the distal portion may be substantially ovaloid when viewed from a distal end of the device. The proximal portion may define a proximal outer diameter, the connecting portion may define a transverse outer diameter along a major axis of a cross-section of the connecting portion and a conjugate outer diameter along a minor axis of a cross-section of the connecting portion, and the distal portion may define a transverse outer diameter along a major axis of the ovaloid and a conjugate outer diameter along a minor axis of the ovaloid. In some cases, the transverse outer diameter of the connecting portion may be smaller than the proximal outer diameter and the conjugate outer diameter of the distal portion. Furthermore, the distal portion may define an overhang region, and/or the proximal portion may define an overhang region. The transverse outer diameter of the connecting portion may be substantially equal to the conjugate outer diameter of the connecting portion. In some embodiments, the first and second outer parts of the distal portion may be disposed at opposite ends of the major axis. Each of the first and second outer parts of the distal portion may comprise a bend in some cases or a curve in other cases.

The occluding device may further comprise an inner layer and an outer layer, wherein the inner and outer layers define at least one of the proximal portion, the connecting portion, or the distal portion. The outer layer may be softer than the inner layer. In some cases, the occluding device may also include a supplementary layer associated with at least one of the proximal portion, the connecting portion, or the distal portion.

In other embodiments, a device for treating a target site is provided that includes a proximal portion, a distal portion, and a connecting portion extending between the proximal portion and the distal portion. The distal portion may define a central part and first and second outer parts extending from the central part. The central part may define a plane, and each of the first and second outer parts may extend distally out of the plane. Furthermore, the proximal portion, the connecting portion, and the distal portion may comprise an inner layer and an outer layer, and the inner layer may define a waist within the connecting portion having a diameter that is smaller than an outer diameter defined by the outer layer in the connecting portion.

In still other embodiments, a device for occluding a septal defect is provided, wherein the device is configured to be constrained to a contracted state and to assume an expanded state when unconstrained. The occluding device may comprise a proximal portion, a distal portion coaxial with the proximal portion, and a connecting portion extending between the proximal portion and the distal portion. In the expanded state, the proximal portion may be substantially circular when viewed from a proximal end of the device and may define a proximal outer diameter. In the expanded state, the distal portion may be substantially ovaloid when viewed from a distal end of the device and may define a transverse outer diameter along a major axis of the ovaloid and a conjugate outer diameter along a minor axis of the ovaloid. In addition, in the expanded state, the connecting portion may define a transverse outer diameter along a major axis of a cross-section of the connecting portion and a conjugate outer diameter along a minor axis of a cross-section of the connecting portion. The distal portion, in the expanded state, may define an overhang region configured to engage and conform to a septal wall surface when the device is disposed within the septal wall.

In some cases, the proximal portion, the connecting portion, and the distal portion are coaxial with each other. In other cases, one of the proximal portion or the distal portion is coaxial with the connecting portion. The occluding device may further include an inner layer and an outer layer, and the inner and outer layers may define at least one of the proximal portion, the connecting portion, or the distal portion. The inner and outer layers may define at least the connecting portion, and the inner layer may define a waist within the connecting portion having a diameter that is smaller than an outer diameter defined by the outer layer in the connecting portion.

The occluding device may also include a proximal end feature fixed to the proximal portion of the occluding device and a distal end feature fixed to the distal end of the occluding device so as to couple the layers together. At least one of the proximal or distal end features may be configured to releasably attach the occluding device to a delivery device. At least one of the proximal or distal end features may comprise an alignment feature that is configured to engage a corresponding alignment feature of the delivery device to limit rotation of the occluding device with respect to the delivery device.

In some cases, the occluding device may include a supplementary layer associated with at least one of the proximal portion, the distal portion, or the connecting portion. The inner layer may define a waist in the connecting portion, and the supplementary layer may be substantially circular and may define a slit and a circumferential fold. The slit may be configured to engage the inner layer proximate the waist such that a folded edge of the supplementary layer approximates a cylindrical configuration of the outer layer in the connecting portion.

In still other embodiments, a device for treating a target site is provided that includes an outer layer and an inner layer disposed within the outer layer. The inner and outer layers may define a proximal portion that is substantially circular when viewed from a proximal end of the device. The inner and outer layers may also define a distal portion coaxial with the proximal portion, and the distal portion may be substantially ovaloid when viewed from a distal end of the device. Furthermore, the inner and outer layers may also define a connecting portion extending between the proximal portion and the distal portion that is coaxial with the proximal and distal portions. The device may, in some cases, include a supplementary layer associated with at least one of the proximal portion, the distal portion, or the connecting portion, and the supplementary layer may include a polymeric material.

In still other embodiments, a device for occluding a septal defect is provided, wherein the device is configured to be constrained in a contracted state and to assume an expanded state when unconstrained. The occluding device may comprise an outer layer and an inner layer disposed within the outer layer. The inner and outer layers may define a proximal portion that is substantially circular when viewed from a proximal end of the device, a distal portion that is substantially ovaloid when viewed from a distal end of the device, and a connecting portion extending between the proximal portion and the distal portion. The distal portion may define a central part and first and second outer parts extending from the central part. The central part may define a plane, and each of the first and second outer parts may extend distally out of the plane. The occluding device may be configured to be received within a delivery device in a contracted state and may be configured to self expand to the expanded state when deployed from the delivery device such that each of the proximal portion and the distal portion engages a corresponding septal wall surface and the connecting portion is disposed within the septal wall.

In still other embodiments, a method of occluding a septal defect is provided. An occluding device configured to be constrained in a contracted state and to assume an expanded state when unconstrained may be initially provided, where the occluding device includes a proximal portion, a distal portion, and a connecting portion extending between the proximal portion and the distal portion. In the expanded state, the distal portion may define a central part and first and second outer parts extending from the central part, wherein the central part defines a plane, and wherein each of the first and second outer parts extends distally out of the plane. The occluding device may be received in the contracted state within a delivery device, and a distal end of the delivery device may be positioned proximate a septal defect. The occluding device may be deployed from the delivery device, such that each of the proximal portion and the distal portion engages a corresponding septal wall surface and the connecting portion is disposed within the septal wall.

In some cases, the occluding device may further include an inner layer and an outer layer that define at least the connecting portion, wherein the inner layer defines a waist within the connecting portion having a diameter that is smaller than an outer diameter defined by the outer layer in the connecting portion. The occluding device may be deployed from the delivery device such that the outer layer in the connecting portion engages the septal wall.

BRIEF DESCRIPTION OF THE DRAWINGS

The foregoing features and advantages of embodiments of the invention will become apparent to those skilled in the art from the following detailed description of a preferred embodiment, especially when considered in conjunction with the accompanying drawings in which like numerals in the several views refer to corresponding parts.

FIG. 2 is a schematic illustration of an occluding device in an expanded state according to an exemplary embodiment;

FIG. 10 is an illustration of an occluding device in an expanded state that is engaged with a delivery device according to an exemplary embodiment;

FIG. 10A is a detail view of an alignment feature of the occluding device of FIG. 10;

FIG. 10B is a detail view of an alignment feature of the delivery device of FIG. 10;

DETAILED DESCRIPTION

Figure 1A:
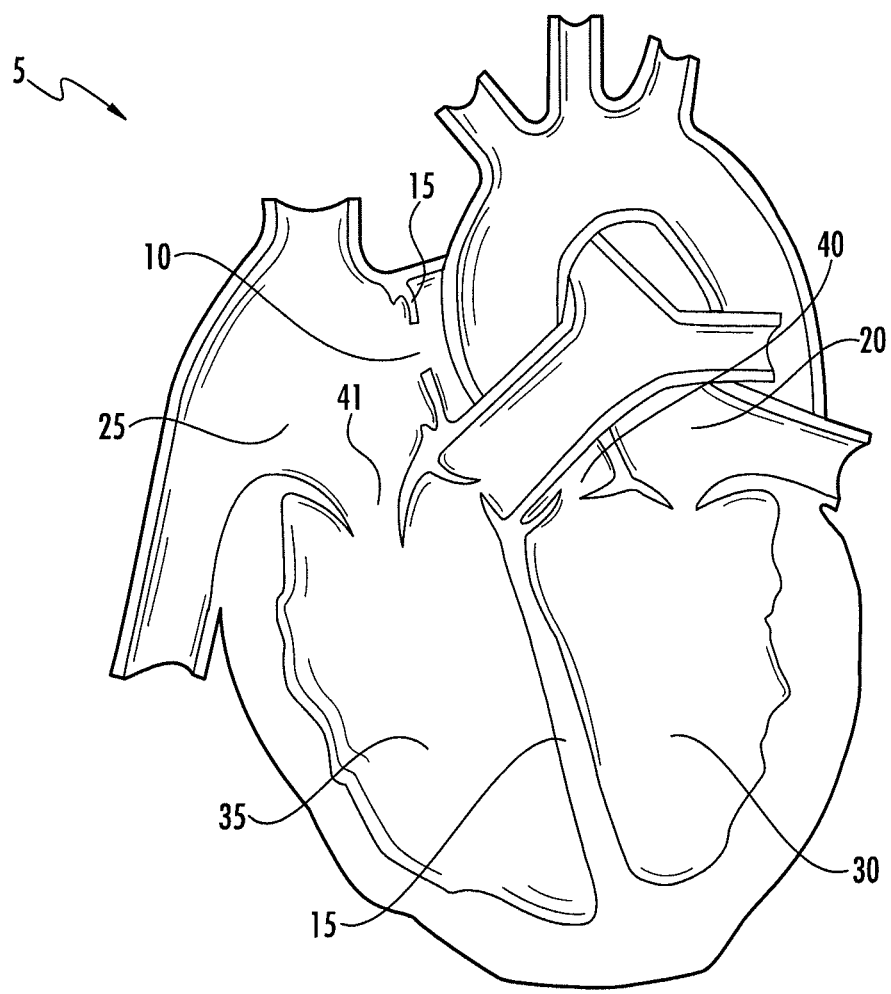
FIG. 1A is an illustration of an atrial septal defect.

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Embodiments provide a device for occluding a septal defect. As described in greater detail below, the occluding device generally has a contracted state for allowing the device to be received within a delivery device for deployment to the site of the defect and an expanded state that is achieved when the device is deployed from the delivery device. The device has a proximal portion, a distal portion concentric with the proximal portion, and a connecting portion extending between the proximal and distal portions. In some embodiments, the proximal portion may be substantially circular, and the distal portion may be substantially ovaloid. Furthermore, in some embodiments, the distal portion has outer parts that bend or curve away from a plane defined by a central part of the distal portion. In this way, the proximal and distal portions may more fully engage and conform to the corresponding septal wall surfaces when the connecting portion is disposed within the septal defect such that proper positioning of the occluding device is maintained with respect to the defect without interfering with the functioning of adjacent heart structures or the blood flow within.

Conventional occluding devices typically have an expanded state and a contracted state for delivery through a catheter to a target site within the body (e.g., the site of the septal defect). For example, the occluding device may have a predetermined shape and may be collapsed by longitudinally stretching the device and inserting the device into the lumen of a delivery device (e.g., a guide catheter or delivery sheath) to constrain the occluding device in a contracted state. The delivery device may then be positioned and advanced in a patient's body such that the distal end of the delivery device is adjacent to the target site.

Once the delivery device is in position at the target site, the occluding device may be advanced through the delivery device and out the distal end of the delivery device, whereupon it may substantially return to its expanded state. The delivery device may then be removed from the patient's body leaving the occluding device positioned to occlude the target site.

It is understood that the use of the term "target site" is not meant to be limiting, as the device may be configured to treat any target site, such as an abnormality, a vessel, an organ, an opening, a chamber, a channel, a hole, a cavity, or the like, located anywhere in the body. The target site may be, for example, an abnormal opening in the patient's body, referred to herein as a "septal defect." A septal defect may be an abnormal or otherwise undesirable opening in a blood vessel, an organ, or other body tissues. For ease of explanation, the examples of an atrial septal defect (a hole in the septum dividing a patient's right and left atria) and a ventricular septal defect (a hole in the septum dividing a patient's right and left ventricles) are used herein. These defects can be located on any part of the atrial or ventricular septum.

Figure 1B:
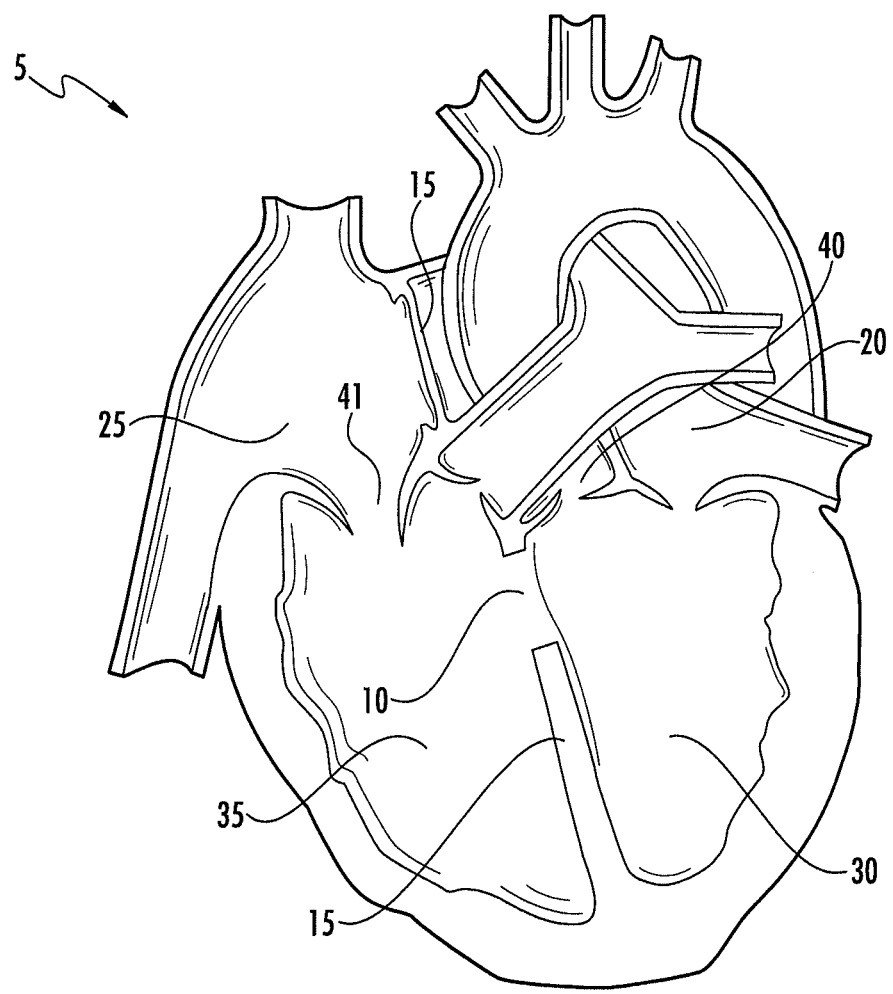
FIG. 1B is an illustration of a ventricular septal defect.

Referring to FIG. 2, an occluding device 100 according to one embodiment is shown. The occluding device 100 includes a proximal portion 105, a distal portion 110, and a connecting portion 115 that extends between the proximal portion and the distal portion. As used herein, the term "proximal" refers to a part of the occluding device 100 that is closest to the operator (e.g., the surgeon or interventionalist) when the device is being delivered through the delivery device, and the term "distal" refers to a part of the occluding device that is farther from the operator. Thus, in the context of an atrial septal defect or a ventricular septal defect and with reference to FIGS. 1A and 1B, the proximal portion 105 is the portion of the occluding device 100 that is nearest the right atrium 25 or the right ventricle 35, respectively, and the distal portion 110 is the part of the occluding device that is nearest the left atrium 20 or the left ventricle 30, respectively, when the occluding device 100 has been placed in the defect 10.

As noted above, the occluding device 100 may be configured to be constrained to a contracted state and to assume an expanded state when unconstrained. For example, in FIGS. 2 and 3, the device 100 is shown in an expanded state, whereas in FIG. 4, the device is shown in a partially contracted state. The occluding device 100 may be in the contracted state, for example, when the ends of the device are pulled away from each other and a radial constraint is applied to the device. In other words, the application of a tensile force F on the ends of the device 100 may serve to collapse the overall diameter d of the device such that it may be received within a delivery device in the contracted state for delivery to the target site. Thus, in this example, the delivery device (e.g., a catheter) applies the radial constraint to maintain the occluding device 100 in the contracted state.

Figure 3:
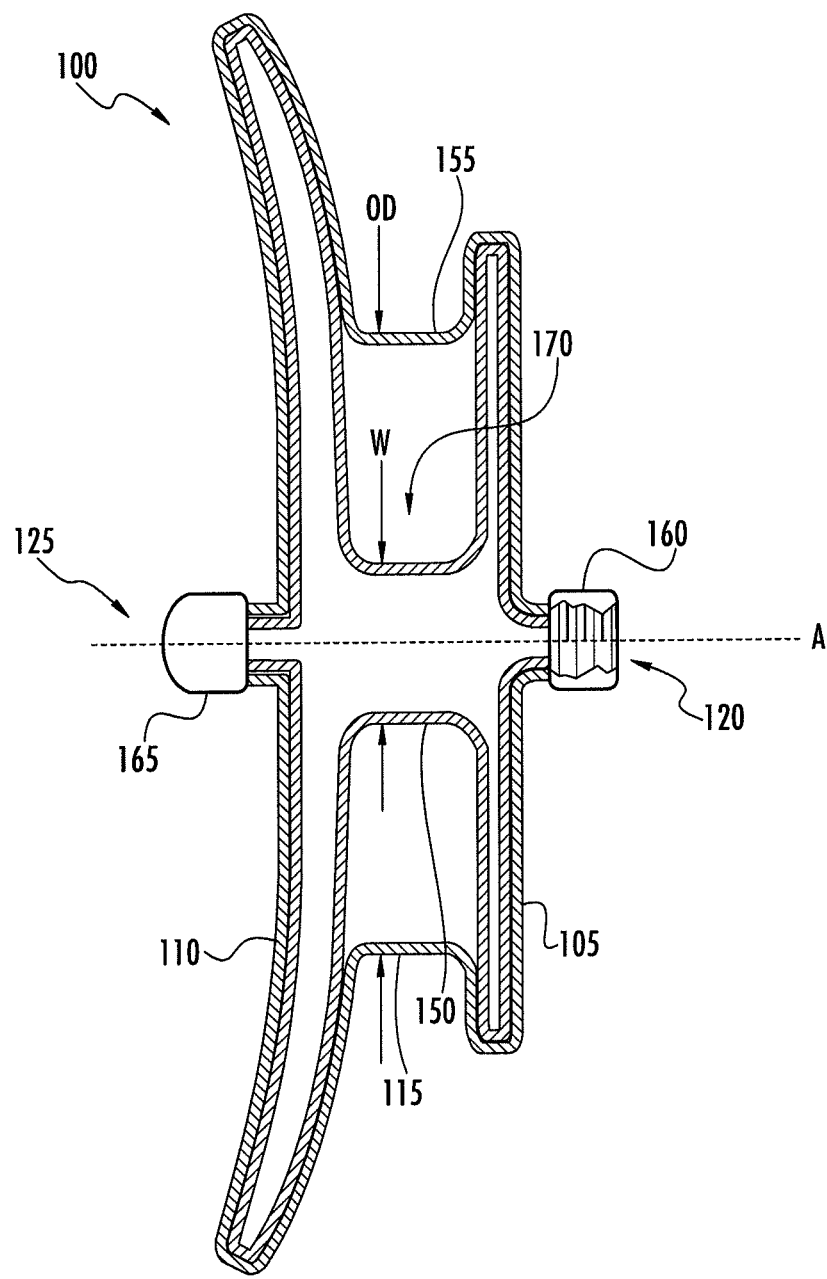
FIG. 3 is a cross-sectional illustration of an occluding device in an expanded state having an inner layer and an outer layer according to an exemplary embodiment.

The occluding device 100 may be configured, however, such that, when the radial constraint is removed, the device can self-expand to the expanded state shown in FIG. 3. For example, as the occluding device 100 is unsheathed from the delivery device, portions of the occluding device that are no longer constrained by the delivery device may self expand, and once the occluding device has been fully deployed from the delivery device proximate the target site, the occluding device will at least partially assume the expanded state.

The properties that allow the occluding device 100 to self-expand from the contracted state to the expanded state may be imparted through proper selection of the materials for making the device as well as through the manufacturing process. The occluding device 100, in some cases, may be formed by braiding, interweaving, knitting, or otherwise combining filamentary materials together, such as by using a braiding machine. These filamentary materials may include, for example, fibers, thread, yarn, cable, metallic wires, polymer strands, and combinations of these materials, any of which are referenced herein as "strands," and such terms may be used interchangeably. The strands may be comprised of any material, such as natural materials, polymers, metals, metallic alloys, or combinations of the same. In some applications, wire strands may be used. The wire strands may be formed of a material that is both resilient and can be heat treated to stabilize the occluding device 100 (e.g., to substantially set a desired shape or braid pattern). The braid of the occluding device 100 may be chosen to have a predetermined pick and pitch to define openings or fenestrations so as to vary the impedance of blood flow therethrough.

Because the occluding device is delivered to a target site in the body in a reduced profile configuration and subsequently allowed to self-expand after being released from the constraint, stainless steel, other metallic alloys, highly elastic alloys, and/or shape memory alloys may be used that are both resilient and can be heat treated to substantially set a desired shape. Exemplary suitable materials may include, for example, cobalt-based low thermal expansion alloys referred to as Elgiloy® Co—Cr—Ni alloy, nickel-based high temperature high-strength "superalloys" (for example, alloys commercially available from Haynes International under the trade name Hastelloy® alloy), nickel-based heat treatable alloys (for example, alloys commercially available from International Nickel under the trade name Incoloy® alloy) and a number of different grades of stainless steel.

In some embodiments, a factor in choosing a suitable material for the strands is the ability of the strands to retain a suitable amount of the deformation induced by the molding surface when subjected to a predetermined heat treatment, such as is exhibited by shape-memory alloys. One type of shape memory alloy is nickel-titanium (NiTi) alloy, called Nitinol alloy, which is also very elastic. For example, this elasticity may allow the occluding device 100 to return to a preset expanded configuration as described herein (shown in FIG. 3) from a contracted configuration (shown in FIG. 4) once it is deployed from a delivery device and is no longer constrained. Accordingly, in some embodiments, at least some of the strands comprise a shape memory alloy. Other materials having elastic properties may also be used, such as spring stainless steel and alloys such as Elgiloy®, Hastelloy®, Phynox®, MP35N®, and CoCrMo alloys.

In some instances, polymeric materials may also be used for the strands. Furthermore, polymeric materials may be combined with other materials in the formation of occluding devices for certain applications. For example, in some cases, the occluding device 100 may include a combination of polyamide strands and stainless steel wire. In other cases, materials may be used that are compatible with magnetic resonance imaging (MRI), considering that some materials may generate heat or experience torque as a result of undergoing MRI or may distort the MRI image. Thus, metallic and/or non-metallic materials that reduce or eliminate the potential problems resulting from the use of MRI may be used, depending on the application.

As noted above, at least portions of the occluding device 100 may possess certain occlusive properties, for example, allowing the device to impede the flow of blood therethrough so as to facilitate thrombosis. As used herein, "substantially preclude or impede flow" shall mean, functionally, that blood flow may occur for a short time, e.g., about 5-60 minutes through the occlusive material, but that the body's clotting mechanism or protein or other body deposits on the strands of at least certain portions of the occluding device 100 results in complete or almost complete occlusion or flow stoppage after this initial time period.

Further examples of materials and manufacturing methods for occluding devices with shape memory properties are provided in U.S. Publication No. 2007/0265656 titled "Multilayer Braided Structures for Occluding Vascular Defects" and filed on Jun. 21, 2007, which is incorporated by reference herein in its entirety.

Figure 5:
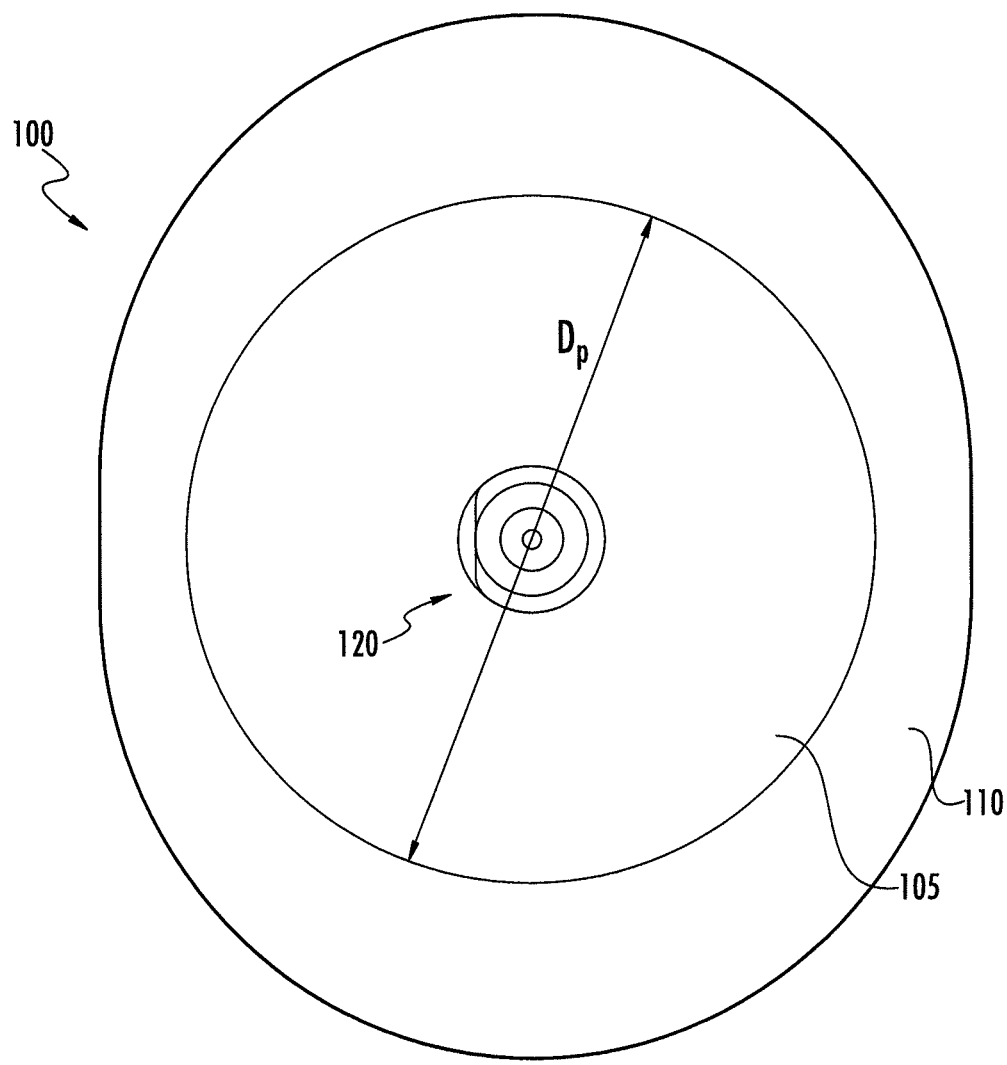
FIG. 5 is a plan view of the proximal end of an occluding device in an expanded state according to an exemplary embodiment.
Figure 6:
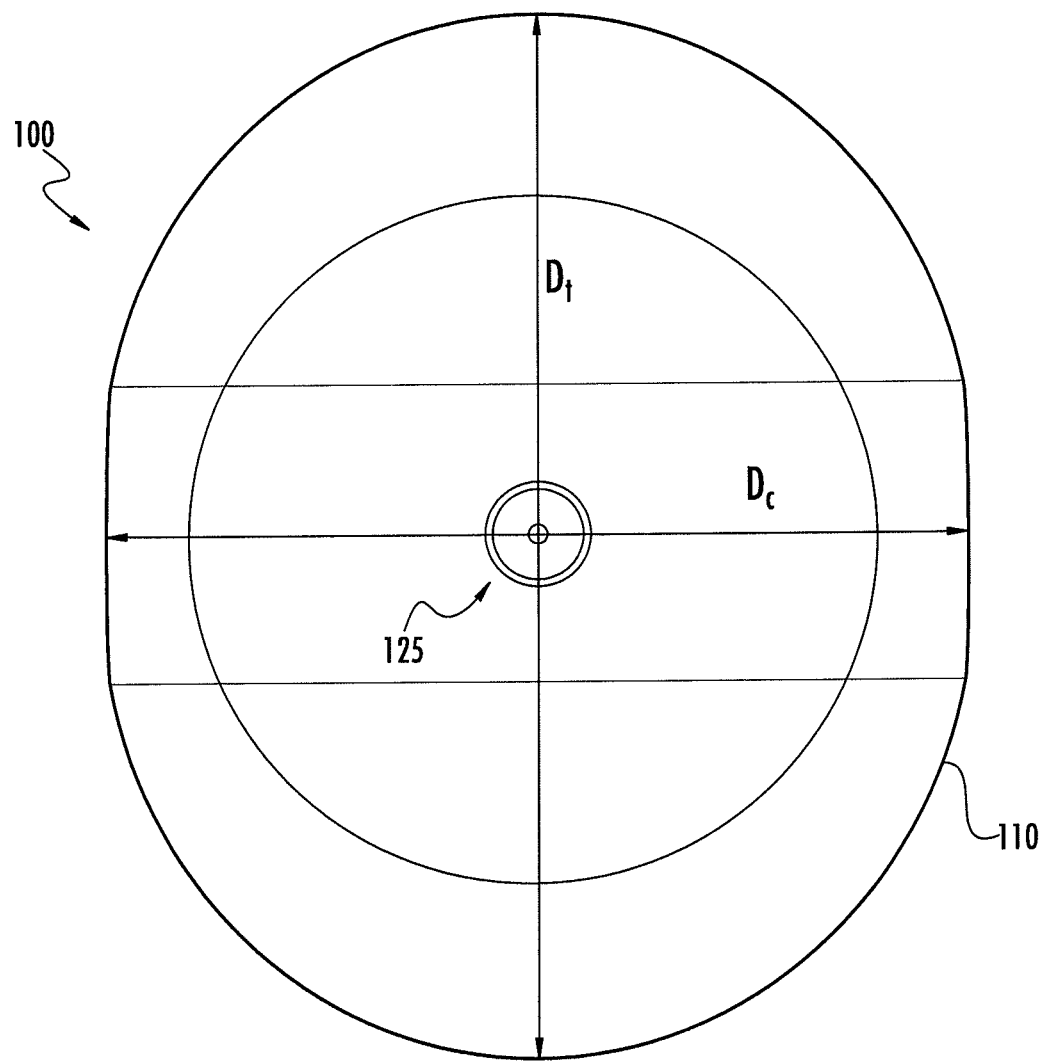
FIG. 6 is a plan view of the distal end of an occluding device in an expanded state according to an exemplary embodiment.
Figure 7:
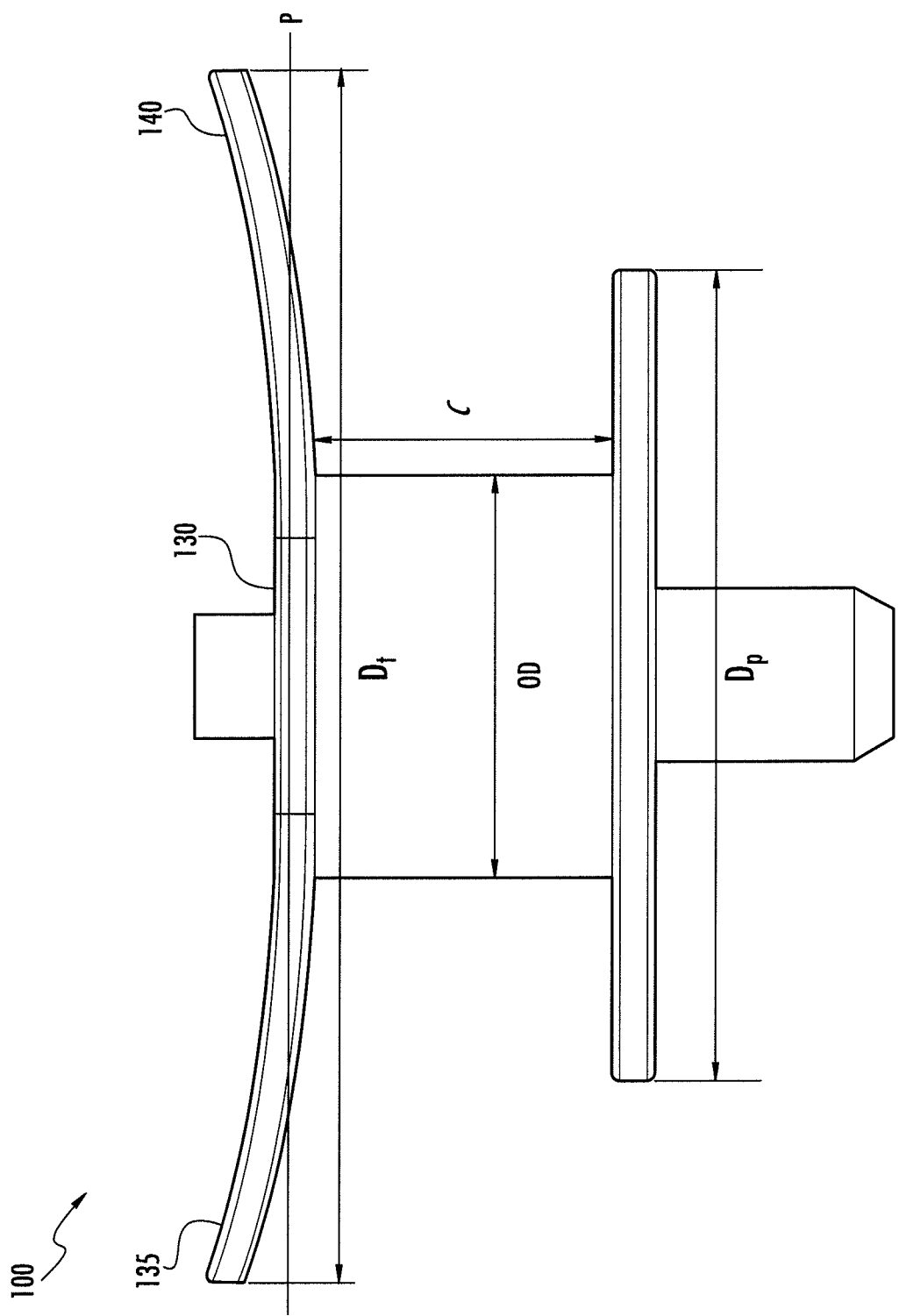
FIG. 7 is a side view of an occluding device with curved first and second outer parts in an expanded state according to an exemplary embodiment.

Referring to FIGS. 2 and 5, in the expanded state, the proximal portion 105 may be substantially circular when viewed from a proximal end 120 of the device 100. The proximal portion 105 may thus define a proximal outer diameter $D_p$. The distal portion 110, on the other hand, may be substantially ovaloid, or have an oval-looking shape, in the expanded state when viewed from a distal end 125 of the device 100, as illustrated in FIG. 6. The distal portion 110 may thus define a transverse outer diameter $D_t$ along the major axis of the ovaloid and a conjugate outer diameter $D_c$ along the minor axis of the ovaloid, as shown. In addition, the connecting portion 115 may define an outer diameter OD and a length l in the expanded state, as shown in FIG. 7, for example. The connecting portion 115 may be formed in round or ovaloid configurations. For example, the connecting portion 115 may define a transverse outer diameter along a major axis of a cross-section of the connecting portion and a conjugate outer diameter along a minor axis of a cross-section of the connecting portion. Thus, in some cases, the transverse and conjugate diameters are substantially equal (i.e., the connecting portion 115 is circular, as depicted in FIG. 7).

The outer diameter OD of the connecting portion 115 may be at least as large as the diameter of the opening in the septal wall 15, and the length l may approximate the thickness of the septal wall to be spanned by the occluding device 100. In addition, the center of one or both of the proximal and distal portions 105, 110 may be coaxial with or offset relative to the central axis of the connecting portion 115 and/or each other, thereby allowing occlusion of a variety of septal defects, including membranous type ventricular septal defects, while providing a large enough retention skirt to securely close the abnormal opening in the septum.

Figure 9:
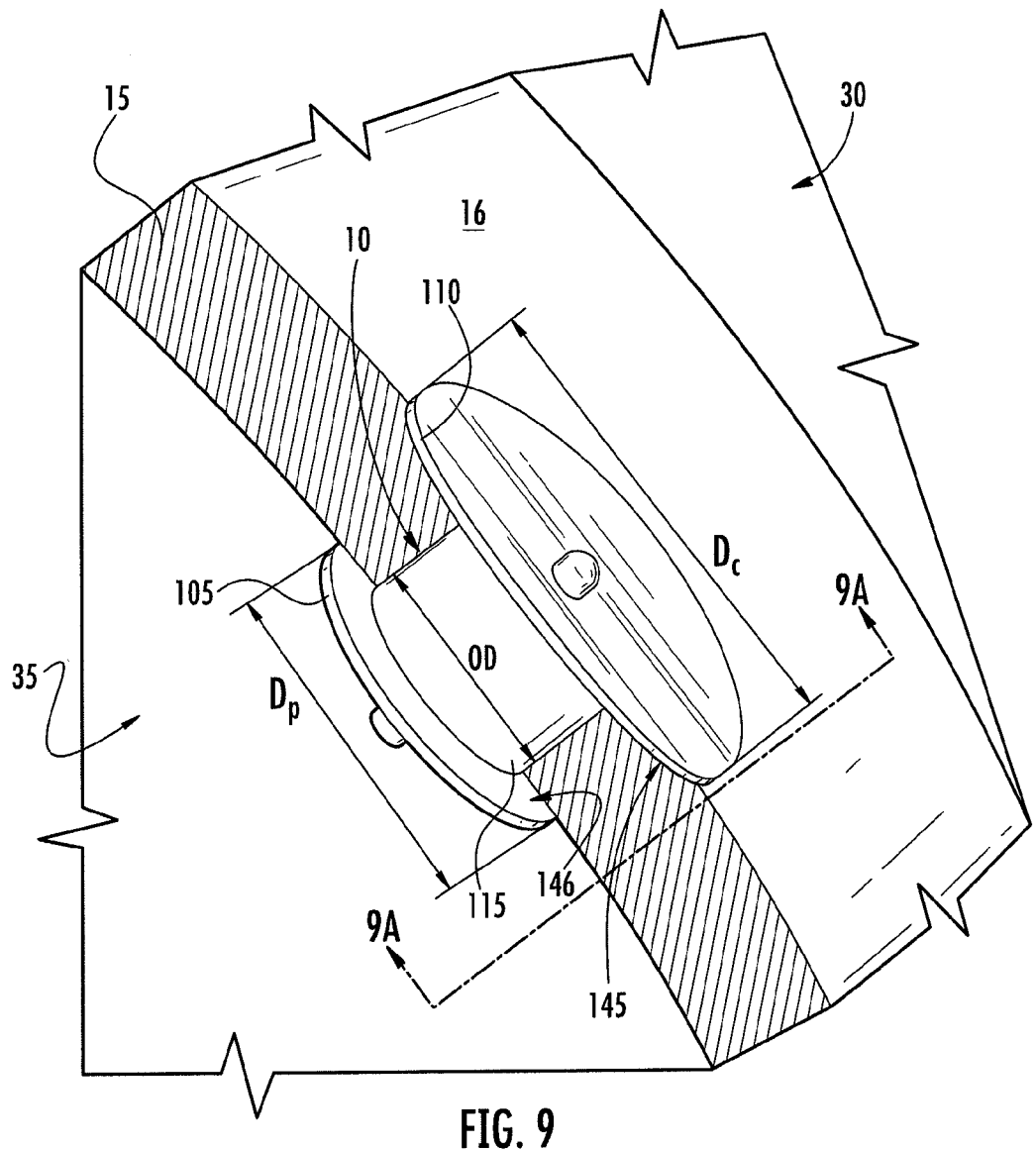
FIGS. 9 and 9A illustrate an occluding device in an expanded state positioned within a septal wall according to an exemplary embodiment.
Figure 9A:
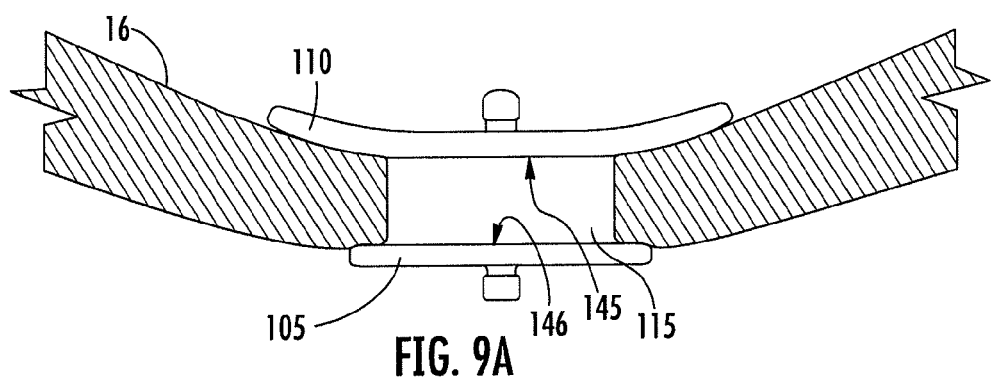

The outer diameter OD (or the transverse outer diameter, in oval configurations) of the connecting portion 115 may be smaller than the proximal outer diameter $D_p$ and the conjugate outer diameter $D_c$, such that when the device 100 is placed in a septal defect and is allowed to self-expand, the proximal portion 105 may engage one septal wall surface and the distal portion 110 may engage another septal wall surface (e.g., corresponding septal wall surfaces on opposite sides of the defective septum). Thus, the connecting portion 115 may be disposed within the septal wall 15, and the proximal and distal portions 105, 110, in a sense, may anchor the connecting portion in place at the target site, as illustrated in FIGS. 9 and 9A. At the same time, however, the oval shape of the distal portion 110 may allow the distal portion to engage the corresponding septal wall 15 over an increased surface area, while avoiding sensitive areas of the surrounding tissue. For example, when used to treat a ventricular septal defect, shown in FIG. 1B, orienting the device 100 as depicted in FIGS. 9 and 9A allows the distal portion 110 to engage the septal wall 15 on the side of the left ventricle 30 with minimal obstruction or interference with, for example, the aortic valve 40.

Figure 8:
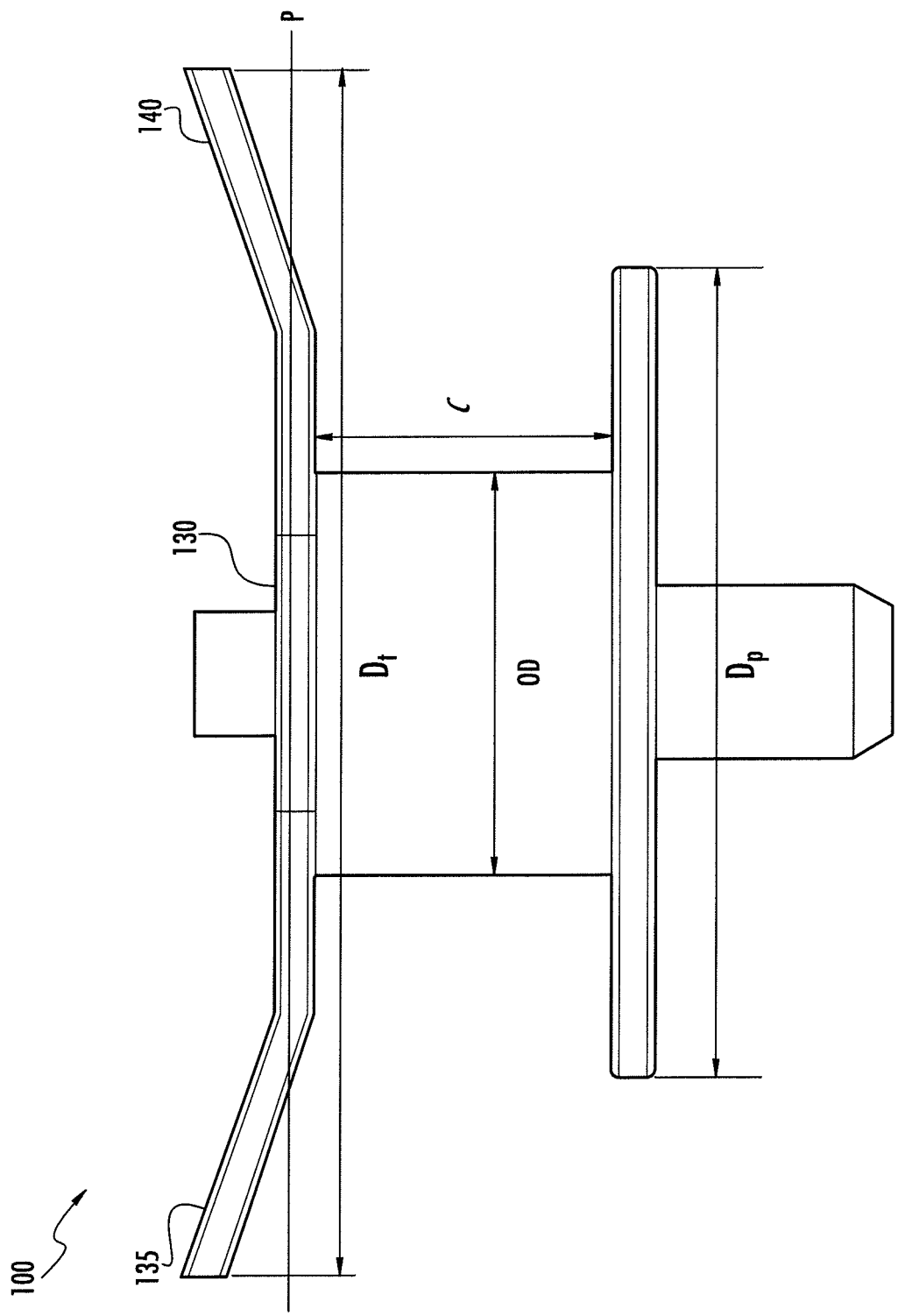
FIG. 8 is a side view of an occluding device with bent first and second outer parts in an expanded state according to an exemplary embodiment.

Turning to FIGS. 2, 7, and 8, in some embodiments, the distal portion 110 defines a central part 130 and first and second outer parts 135, 140 disposed at opposite ends of the major axis of the distal portion (as depicted). Alternatively, the first and second outer parts 135, 140 may be disposed at opposite ends of the minor axis of the distal portion. The central part 130 may define a plane P, as illustrated, and each of the first and second outer parts 135, 140 may extend out of the plane. In this regard, the central part 130 may be substantially flat. In other cases, however, the central part 130 and the first and second outer parts 135, 140 need not be flat, but rather may form a continuous curve, and the plane P may be defined by a single point on the central part (e.g., the most proximal point on the distal portion 110). In some cases, the first and second outer parts 135, 140 may extend distally (i.e., away from the connecting portion 115). Furthermore, the first and second outer parts 135, 140 may comprise a curve in some cases (e.g., shown in FIG. 7) or a bend in other cases (e.g., shown in FIG. 8).

The curved or bent shape of the outer parts 135, 140 may improve the fit with the septal wall at the defect and decrease any localized clamping and/or pinching of the septal tissue that may be associated with the application of the occluding device 100 within the septal wall 15 as compared to prior art devices. The pressure differential across a ventricular septal defect (such as the defect illustrated in FIG. 1B) generally applies force to the distal portion 110 in a direction toward the right ventrical, which could potentially dislodge prior art closing devices. The curvature or bend in the outer parts 135, 140, however, allows the distal portion 110 to fully engage and conform to the corresponding septal wall surface, improving device retention. In addition the force applied to the distal portion 110 does not apply a significant elongation force to the connecting portion 115, which in prior art devices may reduce the diameter of the connecting portion and thus further reduce the radial retention force within the defect itself. Furthermore, because the shape of the distal portion 110 approximates the curvature of the septal wall, any impact or disruption to blood flow within the heart is minimized. In this way, the distal portion 110 may be able to hold the occluding device 100 in place without causing excessive pinching or applying excessive force on the adjacent tissue, such as the His bundle, thereby potentially decreasing the likelihood of heart block and tissue erosion.

In some cases, the transverse outer diameter $D_t$ of the distal portion 110 may be greater than the proximal outer diameter $D_p$ of the proximal portion 105, as shown, for example, in FIG. 7. Furthermore, the conjugate outer diameter $D_c$ of the distal portion 110 may be greater than the outer diameter OD of the connecting portion 115 and, in some cases, also greater than the proximal outer diameter $D_p$ of the proximal portion 105, as shown in FIG. 9.

For example, referring to FIGS. 9 and 9A, the difference between the transverse outer diameter $D_t$ of the distal portion 110 (i.e., along the major axis) and the outer diameter OD of the connecting portion 115 may define an overhang region 145 that is configured to engage the outer surface 16 of the septal tissue. The dimensions of the overhang region 145 may, in some embodiments (e.g., for treating perimembranous ventricular septal defects), vary between approximately 0.5 mm and approximately 3 mm depending on the distance between the defect and the annulus of the aortic valve. In some cases the overhang region 145 may be larger, e.g., up to approximately 15 mm depending on the specific defect being treated and the defect location within the septum, such as in the case of an atrial septal defect where there are larger tissues margins. Furthermore, in some cases, the overhang region 145 may be defined along the minor axis or along both the major and the minor axes of the distal portion 110.

Furthermore, the difference between the proximal outer diameter $D_p$ of the proximal portion 105 and the outer diameter OD of the connecting portion of 115 may define an overhang region 146 that is configured to engage the outer surface of the septal tissue on an opposite side of the septal defect 10, as shown. The dimensions of the overhang region 146 may vary between approximately 0.5 mm and approximately 3 mm and may be approximately 2 mm in applications where a perimembranous septal defect is treated, for example. In cases where the connecting portion 115 is oval, the difference between the conjugate outer diameter $D_c$ of the distal portion 110 and the transverse outer diameter of the connecting portion may define the overhang region 145, and the difference between the proximal outer diameter $D_p$ of the proximal portion 105 and the transverse outer diameter of the connecting portion may define the overhang region 146.

Turning now to FIG. 3, the occluding device 100, in some embodiments, may have an inner layer 150 and an outer layer 155. The inner and outer layers 150, 155 may be concentric and, in some cases, may define one or more of the proximal portion 105, the connecting portion 115, and the distal portion 110. The inner and outer layers 150, 155 may comprise a braided fabric having occlusive properties, as discussed above with respect to the occluding device 100 in general. In this regard, the outer layer 155 may be a relatively soft braided fabric, for example, having a strand diameter of between approximately 0.001 inches and approximately 0.003 inches, as well as a pick count in the range of approximately 30 to approximately 120 picks per inch (PPI) or greater. In general, selecting a smaller strand diameter for the outer layer 155 results in a "softer" feeling device, although the choice of material may also affect the softness of the braid. The inner layer 150, however, may be a stiffer braided fabric, such as a fabric that is made of strands with a diameter of between approximately 0.0015 inches and approximately 0.0035 inches and a pick count between approximately 30 and approximately 120 PPI. In addition, the braid may be configured to expand to the desired maximum diameter of the device when unconstrained, and the PPI of the braids forming the inner and outer layers 150, 155 may be varied to achieve a similar helix length or contracted length.

In this way, the softer fabric of the outer layer 155 may avoid applying excessive radial pressure on the septal tissue (e.g., in the region of the connecting portion 115), while the stiffer braided fabric of the inner layer 150 may provide the device 100 with adequate structural rigidity for maintaining the device in position with respect to the septal defect. This is also due to the inner layer 150 being molded to a smaller diameter than the outer layer 155 in the connecting portion, as described below. For example, an elongation force applied to the inner layer 150 from the distal end 125 of the device should have minimal effect on the retention force within the defect because the inner layer in the connecting portion 115 is sized to have a smaller diameter than the diameter of the defect opening.

The ends of each layer 150, 155 of braided fabric may be welded, soldered, brazed, bonded, clamped, or otherwise held together to keep the braid from unraveling and/or to maintain the relative positions of the inner and outer layers. For example, the respective ends of the inner and outer layers 150, 155 may be held via one or more end features 160, 165. In some embodiments, a proximal feature 160 may be fixed to the proximal end 120 of the occluding device 100, and a distal feature 165 may be fixed to the distal end 125 of the device. For example, the end features 160, 165 may include a recess for receiving the ends of the layers 150, 155, respectively, to keep the layers from moving with respect to each other. In this way, the proximal feature 160 may be used to secure the proximal end of the inner layer 150 to the proximal end of the outer layer 155, and the distal feature 165 may be used to secure the distal end of the inner layer 150 to the distal end of the outer layer 155.

In some cases, at least one of the end features 160, 165 is configured to releasably attach the occluding device 100 to a delivery device. For example, in FIG. 10, an embodiment of the occluding device 100 is shown attached to a multiple tubular catheter delivery system 200 for delivery to the target site. In the depicted embodiment, the proximal feature 160 defines a threaded bore 161 (shown in FIG. 10A) that is configured to receive and engage a threaded distal end of a pusher wire 205 of the delivery device. The occluding device 100 may be configured to travel coaxially within one or more sheaths 210, 215 of the delivery device 200 when the proximal feature 160 is engaged with the threaded end of the pusher wire 205, i.e., traveling with and being moved by the pusher wire. In this way, the occluding device 100 may be introduced into the patient's body and may be moved into position proximate the target site via movement of the delivery device 200. Once the occluding device 100 has been deployed and has achieved the desired position (e.g., at the septal defect), the threads 161 may be disengaged, and the delivery device 200 may be retracted from the patient's body, leaving the occluding device 100 in place.

In some embodiments, at least one of the proximal and distal end features 160, 165 is configured to limit and/or purposefully cause rotation of the occluding device 100 with respect to the delivery device 200. Limited rotation may be useful for initial delivery into position and deployment. Purposeful rotation may be useful for making fine adjustments to the device orientation, depending on the specific patient and defect anatomy and location.

For example, referring to FIGS. 10, 10A, and 10B, the proximal feature 160 may include an alignment feature 162 (such as a "D"-shaped end, as shown) that is configured to engage a corresponding alignment feature 220 of the delivery device (such as a corresponding "D"-shaped end of an intermediate sheath 210 of the delivery device 200). Because, in this example, the proximal feature 160 and the intermediate sheath 210 of the delivery device 200 are configured to engage each other in a particular orientation, the rotational position of the occluding device 100 may be substantially fixed with respect to the delivery device once the occluding device has been threaded onto the pusher wire 205 and engaged with the alignment feature 220. In this way, the medical practitioner can achieve the desired rotational position of the device 100 at the target site (e.g., orienting the first and second outer parts 135, 140 of the ovaloid distal portion 110 so as to avoid the aortic valve in a ventricular septal defect repair). Further details regarding embodiments of the delivery device 200 are included in the co-pending application titled Device and Method for Delivering a Non-Symmetric Vascular Device, filed concurrently herewith, the contents of which are incorporated by reference herein.

Figure 4:
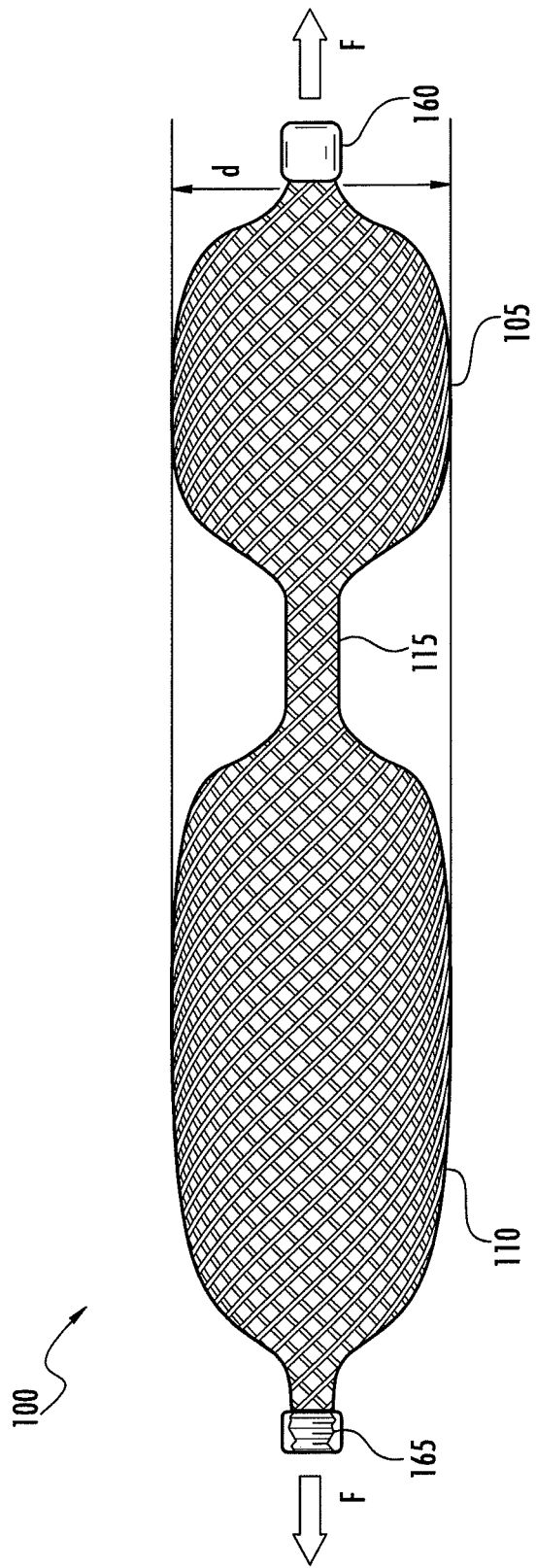
FIG. 4 is a schematic illustration of an occluding device in a contracted state according to an exemplary embodiment.

Accordingly, in some embodiments, the occluding device 100 is configured to be releasably attached to the delivery device 200 in a particular rotational orientation with respect to the delivery device. The occluding device 100 may be constrained by the inside diameter of an outer sheath 215 of the delivery device 200 and may thus be in a contracted state during delivery to the target site (as shown in FIG. 4). As noted above, a threaded pusher wire 205 may be used in conjunction with an intermediate sheath 210 to advance the occluding device 100 along the outer sheath 215 once the delivery device 200 is in position proximate the target site. Thus, at the target site, the occluding device 100 may be deployed by continuing to advance the threaded pusher wire 205 and/or the intermediate sheath 210 toward the open (distal) end of the outer sheath 215. When the occluding device 100 is no longer constrained by the outer sheath 215, the device may self-expand to assume its preset shape in the expanded state, and the compressed distal portion 110 may assume its expanded oval shape, as shown in FIG. 3. As the device 100 continues to be deployed, the connecting portion 115 and the proximal portion 105 may also self-expand to their respective expanded states.

In some cases, the occluding device 100 is allowed to self-expand to its expanded state distally of the septal defect. At that point, the medical practitioner may orient the device 100 as desired, for example, by rotating the intermediate sheath 210 that is attached to the occluding device via the respective alignment features 162, 220 while observing radiopaque images of the device to determine when the device is in the appropriate position. In this regard, the occluding device 100 may include at least one radiopaque marker fixed to one or more of the proximal portion 105, the connecting portion 115, and the distal portion 110. For example, a radiopaque marker may be included on the proximal and/or distal end features 160, 165. Once the device 100 is in the desired orientation, the outer sheath 215 may be held in position while the threaded pusher wire 205 is retracted back into the intermediate and outer sheaths 210, 215, drawing the proximal portion 105 and the connecting portion 115 back into the contracted state within the outer sheath. The delivery device 200 may then be moved proximally, such that the distal portion 110 of the occluding device (which is still in the expanded state) may be moved into engagement with the corresponding septal wall surface (see, e.g., FIG. 9). With the distal portion 110 in place, the intermediate sheath 210 may be held in position while the outer sheath 215 is further withdrawn to deploy the connecting portion 115 within the septal wall 15 and to deploy the proximal portion 105 so that the proximal portion can self-expand and engage the corresponding septal wall surface.

To release the occluding device 100 from the delivery device 200, the outer sheath 215 of the delivery device is typically withdrawn a few millimeters, leaving the distal end of the intermediate sheath 210, which is attached to the device, exposed. In this position, the pusher wire 205 inside the intermediate sheath 210 may be rotated to disengage the threaded connection between the proximal end feature 160 of the occluding device 100 and the threaded pusher wire of the delivery device 200. By holding the outer sheath 215 in place and withdrawing the intermediate sheath 210 away from the occluding device 100, the alignment features 162, 220 (e.g., the D-shaped coupling) may be disengaged, and the delivery device 200 may be withdrawn from the patient's body, leaving the occluding device in place at the site of the defect. Alternatively, in some cases, the intermediate sheath 210 may be disengaged from the alignment feature 162 by drawing it backward before the pusher wire 205 is unscrewed to release the device 100. After the device is released, the intermediate sheath 210 and pusher wire 205 may be drawn back into the delivery sheath 200 for removal from the patient, leaving the device in place.

Figure 11:
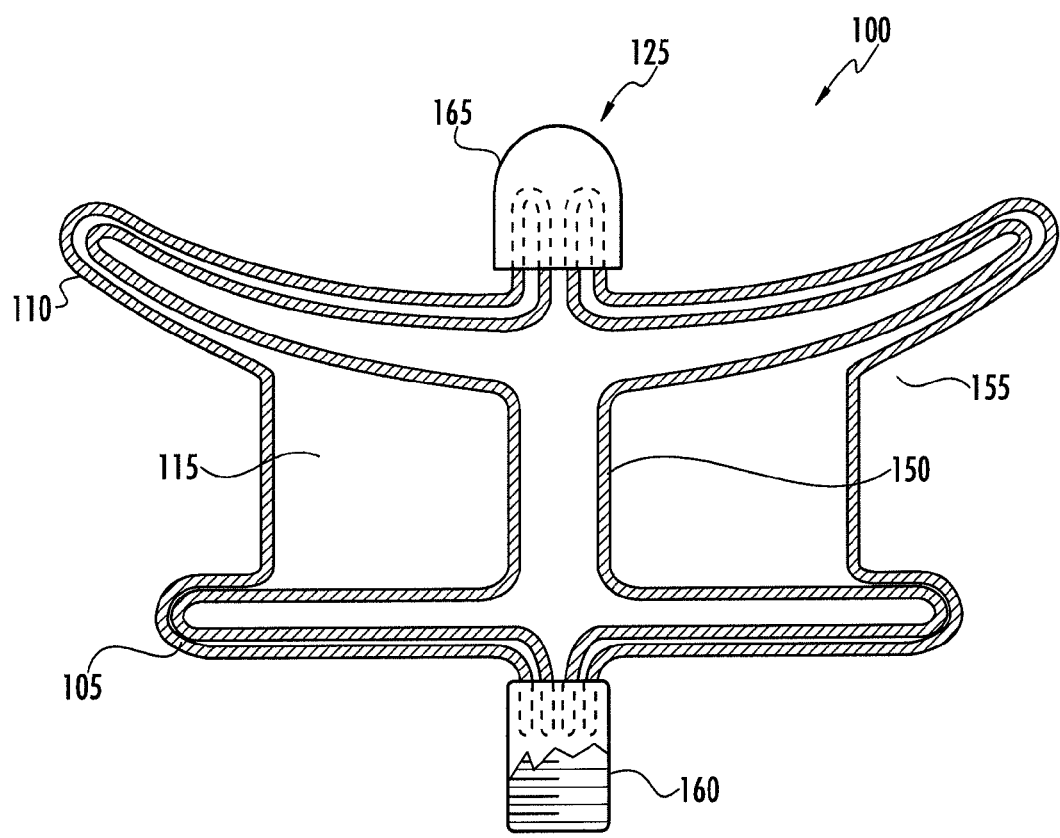
FIG. 11 is a cross-sectional illustration of an occluding device in an expanded state with continuous inner and outer layers according to an exemplary embodiment.

Turning again to FIG. 3, the inner and outer layers 150, 155 may be braided separately (e.g., as separate tubular structures that are subsequently shaped, stabilized, and assembled). Alternatively, the outer layer 155 may be continuously braided with the inner layer 150 in an overlapping configuration. In this case, for example, as shown in FIG. 11, the inner and outer layers 150, 155 may form a continuous braided fabric, with the outer layer being a layer of fabric that is woven over the inner layer starting at the distal end 125, as shown (e.g., an inversion of the inner layer). The common end (i.e., the distal end 125 in the depicted embodiment of FIG. 11) may be clamped, for example, with a distal end feature 165, to strengthen the structure of the distal portion 110 in some embodiments.

With reference to FIG. 3, in some cases, the inner layer 150 defines a waist 170 within the connecting portion 115 having a diameter W at its narrowest circumference that is smaller than the outer diameter OD defined by the outer layer 155 in the connecting portion. In other words, the inner layer 150 and the outer layer 155 are spaced apart within at least part of the connecting portion 115. For example, the waist 170 may form a concave surface about a longitudinal axis A of the device 100. The smaller diameter W of the waist 170 may promote adequate clamping of the proximal and distal portions 105, 110 about the septal defect, for example, through the use of more rigid (less elastic) materials (such as stainless steel), larger diameter wires, wires that have been heat-treated to have a high elastic modulus, and/or wires braided using higher or lower pick counts, which can create a tensile force along the longitudinal axis A of the device 100 and cause each of the proximal and distal portions to more fully engage the corresponding septal wall surface. At the same time, softer, more elastic materials (such as Nitinol), smaller diameter wires, wires heat-treated to have a lower elastic modulus, and/or wires braided using higher or lower pick counts may be used for the outer layer so as to engage the septal wall within the defect opening without exerting excessive radial forces on the surrounding tissue, such as the HIS bundle. Thus the difference between the outer diameter OD and the waist diameter W may create a cushioned zone for engaging the septal wall without substantially impairing the ability of the device 100 to stay in position within the defect. Stated differently, the inner layer 150 may act as a frame for the device 100, expanding the device, facilitating the positioning of the device, and maintaining the device in place after implant by resisting forces within the heart. At the same time, the outer layer 155 may provide soft and comfortable engagement of the device 100 with the tissues within and on both sides of the defect and may further provide a majority of the occlusion within the defect.

In some embodiments, the inner layer 150 is only provided in certain portions of the occluding device 100. For example, with reference to FIG. 12, an inner layer 151, 152 may only be provided in the proximal and distal portions 105, 110 of the occluding device 100. Thus, a first inner layer 151, instead of extending between the proximal and distal portions 105, 110 as shown in FIG. 3, may double back to the proximal end 120 within the proximal portion, and a second inner layer 152 may double back to the distal end 125 within the distal portion. Thus, the proximal end feature 160 in this case may be configured to receive two ends of the first inner layer 151 and one end of the outer layer 155, as shown. Likewise, the distal end feature 165 in this case may be configured to receive two ends of the second inner layer 152 and one end of the outer layer 155. As a result, the connecting portion 115 in such embodiments may comprise a single layer, i.e., the outer layer 155.

Figure 12:
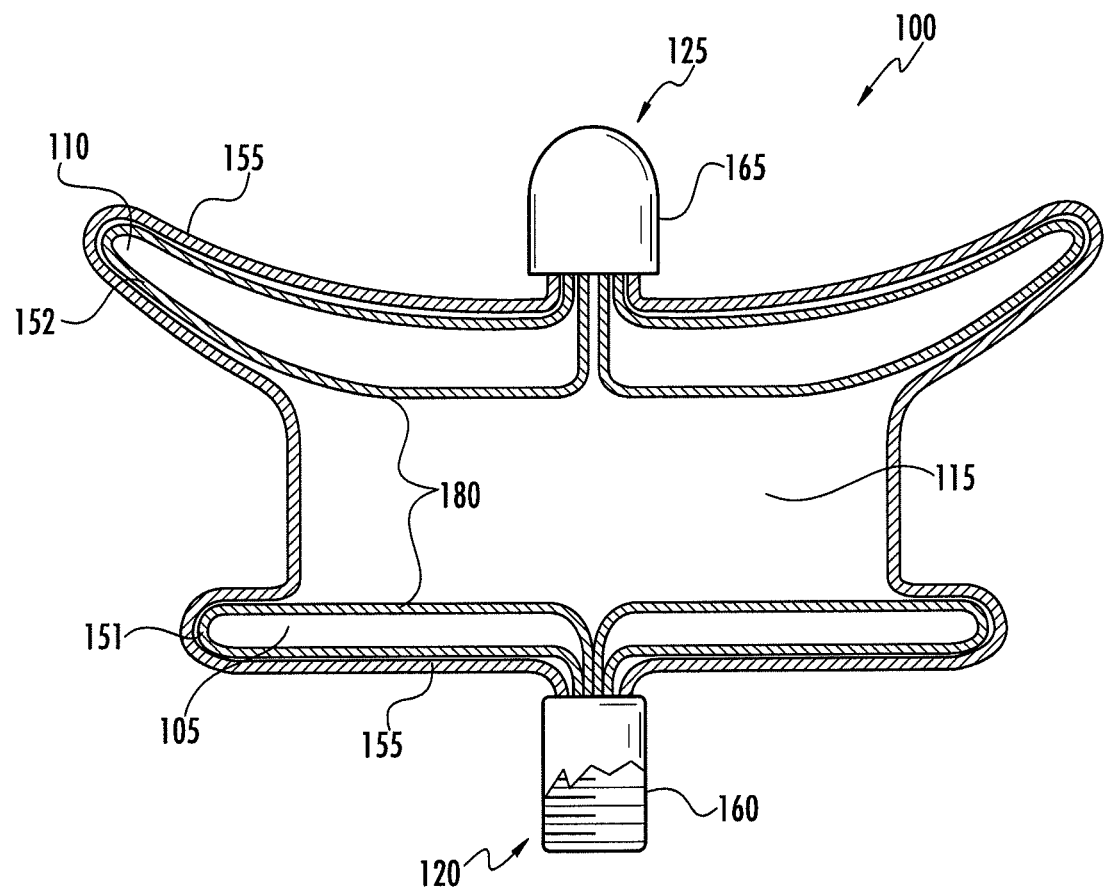
FIG. 12 is a cross-sectional illustration of an occluding device in an expanded state with inner and outer layers in the proximal and distal portions according to an exemplary embodiment.

In some embodiments, the occluding device 100 may include one or more supplementary layers 180 in addition to the inner layer 150 and the outer layer 155. In FIG. 12, for example, the overlapping portions of the first and second inner layers 151, 152 that double back towards an end of the device in the proximal portion 105 and in the distal portion 110 may define a supplementary layer 180. In other embodiments, the supplementary layer 180 may be a separate layer extending between the proximal and distal ends 120, 125 of the device (for example, between the inner and outer layers 150, 155), thereby defining one or more of the proximal, distal, and connecting portions 105, 110, 115.

Figure 13A:
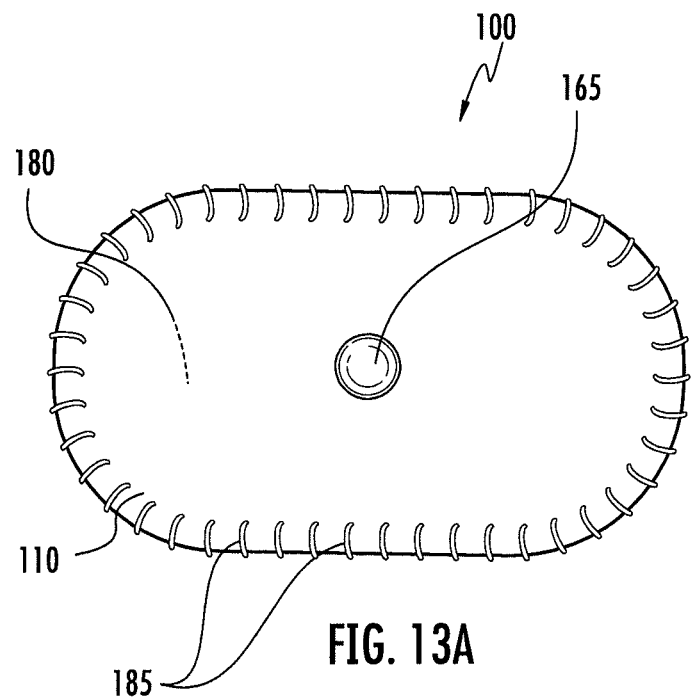
FIG. 13A is an illustration of the distal portion of an occluding device in an expanded state having a sutured supplementary layer according to an exemplary embodiment.

In some cases, the supplementary layer 180 may not extend all the way between the proximal and distal ends 120, 125, but rather may form a patch. In addition, the supplementary layer 180 may include a material such as a metal and/or a polymer to enhance the occlusive properties of one or more areas of the occluding device 100. Referring to FIG. 13A, for example, one or more polyester fabric supplementary layers 180 may be included in the distal portion 110, such as by sewing the polyester fabric to the periphery of the ovaloid distal portion using sutures 185. The sutures 185 may be made using radiopaque filament thread, such as platinum iridium thread, to allow a medical practitioner to view the location of the distal portion 110 within the body using radio fluoroscopy to facilitate proper delivery and positioning of the device.

Figure 13B:
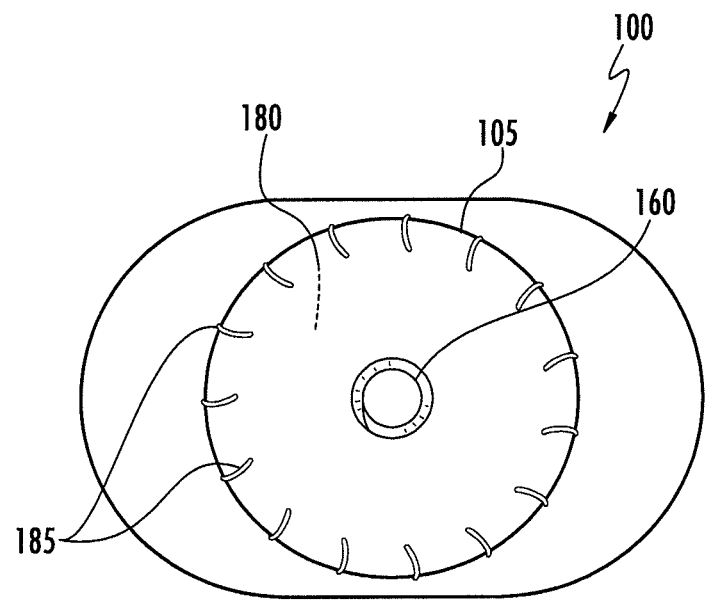
FIG. 13B is an illustration of the proximal portion of an occluding device in an expanded state having a sutured supplementary layer according to an exemplary embodiment.

Alternatively or additionally, as illustrated in FIG. 13B, one or more polyester fabric supplementary layers 180 may be included in the proximal portion 105 of the device 100, e.g., using sutures 185. The shape of the supplementary layers 180 may correspond to the portions of the device in which they are placed, so that supplementary layers placed in the proximal portion 105 may be substantially circular, and supplementary layers placed in the distal portion 110 may be substantially ovaloid. Other polymer or thrombogenic materials may be used in the supplementary layers 180 to enhance the device's occlusive properties.

Figure 14:
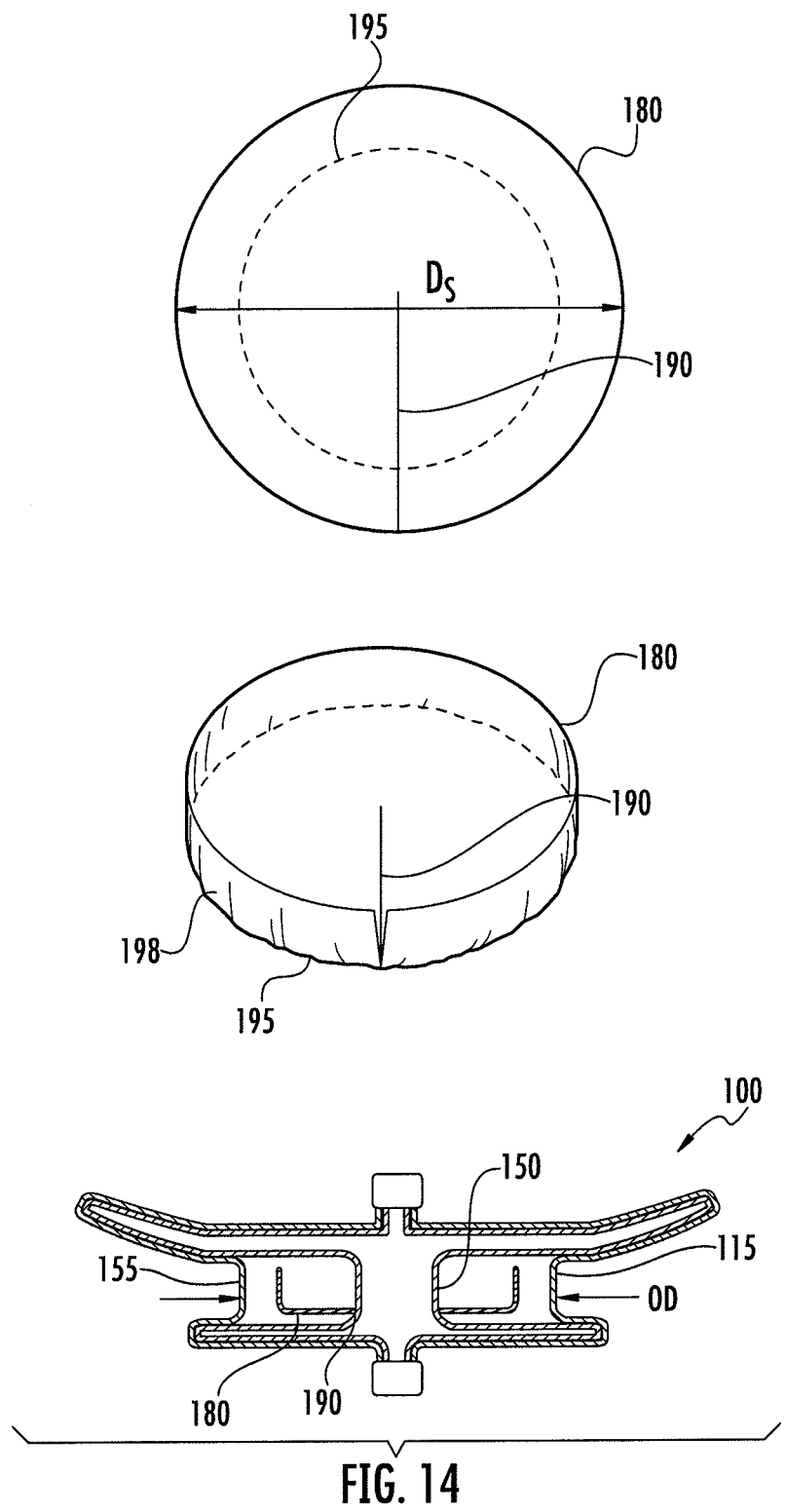
FIG. 14 is a schematic illustration of a supplementary layer configured to be disposed in the connecting portion of an occluding device according to an exemplary embodiment.

In still other embodiments, one or more supplementary layers may be included in the connecting portion 115 of the device 100. For example, as shown in FIG. 14, a supplementary layer 180 may be provided that is configured to fit around the inner layer 150 in the connecting portion 115, that is, between the inner layer and the outer layer 155. In this case, the supplementary layer 180 may be substantially circular and may have a diameter D, that, in its unfolded form, is larger than the outer diameter OD of the connecting portion 115. The supplementary layer 180 may define a slit 190 that extends approximately ⅔ of the diameter of the supplementary layer, such that the supplementary layer may be placed around the inner layer 150 (e.g., proximate the waist 170, shown in FIG. 4) by receiving the inner layer within the slit. A periphery of the supplementary layer 180 may define a circumferential fold (as indicated by dashed lines 195 in FIG. 14), such that the folded edge 198 is at an approximately 90° angle to the mid-portion of the supplementary layer and has a cylindrical configuration that approximates the cylindrical configuration of the outer layer 155 in the area of the connecting portion 115, as shown. Thus, the slit 190 may allow the supplementary layer 180 in this case to accommodate and fit around the inner layer 150 in the region of the connecting portion 115. In some cases, the supplementary layer 180 may be placed within the inner layer 150, as opposed to between the inner and outer layers 150, 155. In any case, the supplementary layer 180 may be attached to one or more of the inner and outer layers 150, 155 using sutures or other appropriate attachment methods.

As noted above, one or more supplementary layers 180 may be used as described above in one or more portions of the occluding device 100 to enhance the ability of the device to slow the flow of fluid (e.g., blood) through the septal defect. In this regard, in some embodiments, one or more of the inner, outer, or supplementary layers 150, 155, 180 may be made using metal, polymer, or a combination of the two. In addition, to enhance the ability of the device 100 to maintain its position in the septal defect, the outer layer 155, the inner layer 150, and/or the supplementary layer 180 may be made of a material such as a shape memory alloy (e.g., Nitinol) or an elastic metal (e.g., nickel titanium), which has a tendency to return to its pre-set shape after being deformed, and may in some cases include a polymeric material such as polyester filaments braided w/Nitinol strands or expanded polytetrafluoroethylene (ePTFE) filaments.

In cases where the inner, outer, or supplementary layers 150, 155, 180 are braided fabrics, certain properties of the occluding device 100 (such as occlusion, stiffness, and clamping force, among others) may be changed or enhanced by modifying one or more braiding parameters. For example, braiding parameters such as the strand diameter, the pitch angle of the braid, the pick count, the number of strands, and/or the heat treatment process used may be changed in one or more layers 150, 155, 180 of the device and/or in one or more portions 105, 110, 115 of the device, according to user preferences and the type of defect to be treated. In one embodiment, for example, the pick count or pitch angle of the inner and outer layers 150, 155 may be different from each other to accommodate the differences in the overall shape of the two layers (such as when the inner layer forms a waist 170 in the region of the connecting portion 115 with a smaller diameter than the corresponding outer diameter OD of the outer layer 155, as shown in FIG. 3). In this way, despite the different shapes of the inner and outer layers 150, 155, the two layers may have generally the same length (i.e., from the distal end 125 to the proximal end 120) when in the contracted state so that no material bunching of the inner and outer layers occurs when the occluding device 100 is received within a delivery system 200 for deployment to the target site, as described above. Similarly, in cases where the inner and outer layers 150, 155 are fabricated by inversion or eversion of a continuously braided fabric, the braiding mandrel diameter, the pick count, and/or the pitch angle may vary as desired from one portion of the tubular braided fabric to another portion of the fabric. In this way, for example, the optimal draw down of the layers (i.e., the reduction in overall diameter d in the contracted state, shown in FIG. 4) may occur during elongation for placement into the delivery device.

An occluding device 100 may be configured according to one or more of the embodiments described above for occluding various types of septal defects. Depending on the type, location, and size of the defect, among other factors, the occluding device 100 may be configured (e.g., sized and shaped) differently to optimize the delivery and/or functioning of the device. For example, referring to FIGS. 3-9A, various dimensions of the device 100 may be adjusted according to the user's needs or preferences.

In some embodiments, for instance, the connecting portion 115 may have an outer surface that is hub-shaped (i.e., tapering in from the ends to a mid-section having a reduced diameter), barrel-shaped (i.e., having an enlarged mid-section with reduced-diameter ends), cylindrical (as shown in FIG. 3), or tapered from one end to the other, depending on the particular configuration of the defect to be spanned. Similarly, the proximal and distal portions 105, 110 may have different sizes ($D_p$, $D_t$, $D_c$) and thicknesses in the expanded state, and the orientation of the proximal and distal portions with respect to each other may be different. For example, in one embodiment, the proximal and distal portions 105, 110 may be substantially parallel to each other, whereas in another embodiment they may be at an angle. The distance between the proximal and distal portions 105, 110, denoted as l in FIGS. 7 and 8, may also vary. In addition, the shape of the proximal portion 105, the distal portion 110, and the connecting portion 115, their relative positions (e.g., partly, fully, or not coaxially aligned), the number of layers, the materials that the layers are made of, the braid pattern, the pick count, the strand diameter, and the number of strands may each be adjusted and varied to suit a particular application. The shape of the proximal portion 105, although depicted as being circular in the figures, may also be oval or have any other desired shape suitable for the specific location, defect configuration, and proximity to adjacent tissue. Similarly, the connecting portion 115 and the distal portion 110 may have shapes that are other than circular or oval, as needed.

An occluding device 100 designed to repair a ventricular septal defect, for example, may have an outer layer 155 made of nickel titanium alloy (e.g., Nitinol) wire strands with a diameter ranging from approximately 0.001 inches to approximately 0.006 inches, such as between approximately 0.00125 inches and approximately 0.003 inches. The wire strands of the outer layer may be braided to form a fabric with a pick count of approximately 30 to approximately 150, such as in the range of approximately 65 to approximately 120, and the number of strands used may be between 36 and 288, such as in the range of 72 to 144 strands. In addition, the outer layer 155 may be braided onto a mandrel having an outer diameter in the range of approximately 4 mm to approximately 25 mm, such as between 8 mm and 22 mm.

Continuing the example above, a particular occluding device 100 for repairing a ventricular septal defect may have an inner layer 150 made of Nitinol wire strands with a diameter ranging from approximately 0.001 inches to approximately 0.004 inches, such as between approximately 0.001 inches and approximately 0.002 inches in diameter. The strands may be braided to form a fabric having a pick count of 30 to 150, such as in the range of 60 to 95, and 36 to 288 strands may be used, such as 72 to 144 strands. The inner layer 150 may be braided onto a mandrel having an outer diameter in the range of approximately 4 mm to approximately 28 mm, such as approximately 4 mm to approximately 20 mm.

For example, a range of approximate values is provided in Table 1, below, for various dimensions of an occluding device 100, such as the device shown in FIGS. 3-7.

TABLE 1

| Dimension | Approximate Range | Description |
|---|---|---|
| $D_t$ | 12-30 mm | Transverse Outer Diameter (major axis of distal portion 110) |
| $D_c$ | 2-23 mm | Conjugate Outer Diameter (minor axis of distal portion 110) |
| $D_p$ | 4-22 mm | Outer Diameter (proximal portion 105) |
| OD | 4-18 mm | Connecting Portion 115 Outer Diameter |
| l | 0.5 mm-10 mm | Connecting Portion 115 Length |
| W | 1-10 mm | Connecting Portion 115 Waist Diameter |

Table 2 provides an example of the dimensions that may be used for a particular occluding device 100 according to the embodiments described above that may be useful for occluding a ventricular septal defect.

TABLE 2

| | | |
|---|---:|---|
| Device Size (nominal) | 4 | mm |
| Outer Layer Strand Diameter | 0.00125 | in |
| Outer Layer Number of Strands | 144 | |
| Outer Layer Mandrel Diameter | 8 | mm |
| Outer Layer Pick Count | 87 | |
| Connecting Portion Outer Diameter (OD) | 4 | mm |
| Connecting Portion Length (l) | 3 | mm |
| Distal Portion Transverse Outer Diameter ($D_t$) | 12 | mm |
| Distal Portion Conjugate Outer Diameter ($D_c$) | 7 | mm |
| Distal Overhang Distance (145) | 3 | mm |
| Inner Layer Strand Diameter | 0.002 | in |
| Inner Layer Number of Strands | 144 | |
| Inner Layer Mandrel Diameter | 9 | mm |
| Inner Layer Pick Count | 89 | |
| Connecting Portion Waist Diameter (W) | 1.5 | mm |

Table 3 provides another example of a particular occluding device 100 according to the embodiments described above that may be useful for occluding a ventricular septal defect.

TABLE 3

| | | |
|---|---:|---|
| Device Size (nominal) | 14 | mm |
| Outer Layer Strand Diameter | 0.0025 | in |
| Outer Layer Number of Strands | 144 | |
| Outer Layer Mandrel Diameter | 22 | mm |
| Outer Layer Pick Count | 69 | |
| Connecting Portion Outer Diameter (OD) | 14 | mm |
| Connecting Portion Length (l) | 3 | mm |
| Distal Portion Transverse Outer Diameter ($D_t$) | 26 | mm |
| Distal Portion Conjugate Outer Diameter ($D_c$) | 17 | mm |
| Distal Overhang Distance (145) | 3 | mm |
| Inner Layer Strand Diameter | 0.003 | in |
| Inner Layer Number of Strands | 144 | |
| Inner Layer Mandrel Diameter | 24 | mm |
| Inner Layer Pick Count | 64 | |
| Connecting Portion Waist Diameter (W) | 6.8 | mm |

Figure 15:
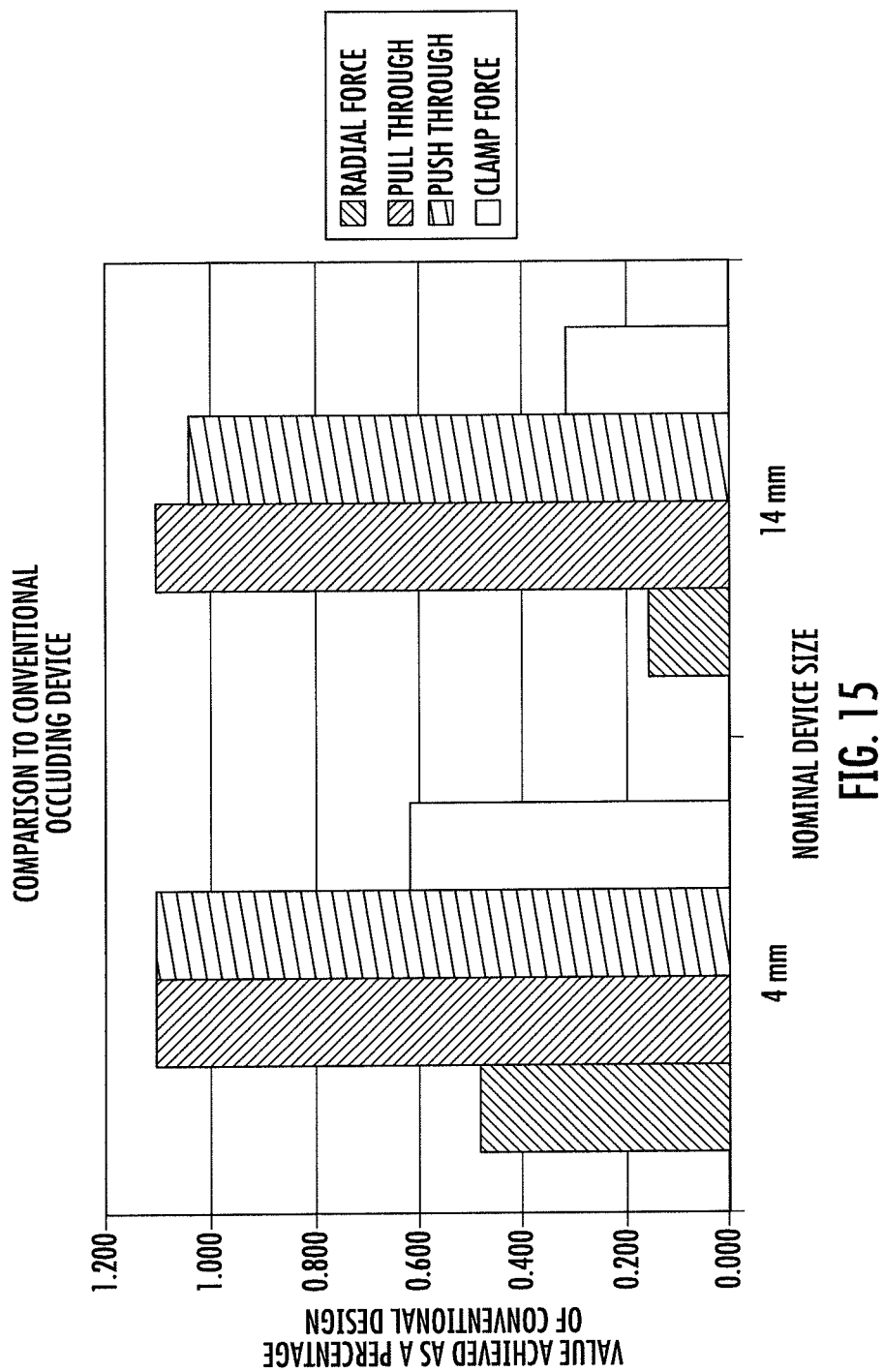
FIG. 15 is a chart illustrating performance parameters of an occluding device according to an exemplary embodiment as compared to a conventional occluding device.

As described above, embodiments of the present invention provide an occluding device that can be positioned at a septal defect, for example, with reduced force on the septal wall tissue and minimal interference with adjacent structures, but at the same time is configured to engage the septal wall securely, minimizing the risk of dislodgement as compared to similarly sized conventional occluding devices. For example, when compared to a single layer occluding device with circular retention skirts that are curved proximally, an occluding device 100 such as the one depicted in FIG. 3 with a nominal size of 4 mm (i.e., having a connecting portion 115 with an OD of 4 mm) exhibits the same or better retention properties (e.g., higher pull-through and push-through performance), but at the same time applies less than half as much force to the septal wall tissue, exerting less radial force and clamp force on the septal wall. Embodiments of an occluding device 100 configured as shown in FIG. 3 with a nominal size of 14 mm may likewise exhibit improved pull-through and push-through performance, but again apply less radial force and clamp force to the septal wall tissue. This improved performance is illustrated in FIG. 15, which shows the performance of the 4 mm and the 14 mm occluding devices of this example as a percentage of the performance of a conventional single layer occluding device having the same nominal size with circular retention skirts that are curved proximally. In this regard, "pull-through" refers to the ability of the device to resist being pulled through the defect during the delivery procedure while the pusher wire is still attached to the device, and "push-through" refers to the ability of the device to resist dislodgement once the device is deployed within the defect and the delivery system is detached This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments, as desired for a particular application, without departing from the scope of this invention.

That which is claimed:

1. A device for occluding a septal defect, wherein the device is configured to be constrained in a contracted state and to assume an expanded state when unconstrained, the occluding device comprising:

a proximal portion comprising a proximal outer diameter;

a distal portion comprising a transverse outer diameter, wherein the transverse outer diameter of the distal portion is greater than the proximal outer diameter of the proximal portion in the expanded state; and a connecting portion extending between the proximal portion and the distal portion, wherein, in the expanded state, the distal portion defines a central part and first and second outer parts extending from the central part, wherein the central part defines a plane, and wherein each of the first and second outer parts extends distally out of the plane, and wherein the occluding device is configured to be received within a delivery device in a contracted state and is configured to self expand to the expanded state when deployed from the delivery device such that each of the proximal portion and the distal portion engages a corresponding septal wall surface and the connecting portion is disposed within the septal wall.

2. The occluding device of claim 1, wherein, in the expanded state, the central part is substantially flat.

3. The occluding device of claim 1, wherein, in the expanded state, the proximal portion is substantially circular when viewed from a proximal end of the device, and the distal portion is substantially ovaloid when viewed from a distal end of the device.

4. The occluding device of claim 3, wherein the connecting portion defines a transverse outer diameter along a major axis of a cross-section of the connecting portion and a conjugate outer diameter along a minor axis of a cross-section of the connecting portion, and the distal portion defines the transverse outer diameter along a major axis of the ovaloid and a conjugate outer diameter along a minor axis of the ovaloid.

5. The occluding device of claim 4, wherein the transverse outer diameter of the connecting portion is smaller than the proximal outer diameter and the conjugate outer diameter of the distal portion.

6. The occluding device of claim 4, wherein the distal portion defines an overhang region.

7. The occluding device of claim 4, wherein the proximal portion defines an overhang region.

8. The occluding device of claim 4, wherein the transverse outer diameter of the connecting portion is substantially equal to the conjugate outer diameter of the connecting portion.

9. The occluding device of claim 1, wherein the first and second outer parts of the distal portion are disposed at opposite ends of the major axis.

10. The occluding device of claim 1, wherein each of the first and second outer parts of the distal portion comprises a bend.

11. The occluding device of claim 1, wherein each of the first and second outer parts of the distal portion comprises a curve.

12. The occluding device of claim 1 further comprising an inner layer and an outer layer, wherein the inner and outer layers define at least one of the proximal portion, the connecting portion, or the distal portion.

13. The occluding device of claim 12, wherein the outer layer is softer than the inner layer.

14. The occluding device of claim 12 further comprising a supplementary layer associated with at least one of the proximal portion, the connecting portion, or the distal portion.

15. A device for treating a target site comprising:
a proximal portion comprising a proximal outer diameter;
a distal portion comprising a transverse outer diameter, wherein the transverse outer diameter of the distal portion is greater than the proximal outer diameter of the proximal portion in the expanded state; and
a connecting portion extending between the proximal portion and the distal portion,
wherein the distal portion defines a central part and first and second outer parts extending from the central part, wherein the central part defines a plane, and wherein each of the first and second outer parts extends distally out of the plane,
wherein the proximal portion, the connecting portion, and the distal portion comprise an inner layer and an outer layer, and
wherein the inner layer defines a waist within the connecting portion having a diameter that is smaller than an outer diameter defined by the outer layer in the connecting portion.

16. A device for occluding a septal defect, wherein the device is configured to be constrained to a contracted state and to assume an expanded state when unconstrained, the occluding device comprising:
a proximal portion, wherein, in the expanded state, the proximal portion is substantially circular when viewed from a proximal end of the device and defines a proximal outer diameter;
a distal portion coaxial with the proximal portion, wherein, in the expanded state, the distal portion is substantially ovaloid when viewed from a distal end of the device and defines a transverse outer diameter along a major axis of the ovaloid and a conjugate outer diameter along a minor axis of the ovaloid; and
a connecting portion extending between the proximal portion and the distal portion, wherein, in the expanded state, the connecting portion defines a transverse outer diameter along a major axis of a cross-section of the connecting portion and a conjugate outer diameter along a minor axis of a cross-section of the connecting portion,
wherein the distal portion, in the expanded state, defines an overhang region configured to engage and conform to a septal wall surface when the device is disposed within the septal wall.

17. The occluding device of claim 16, wherein the transverse outer diameter of the connecting portion is substantially equal to the conjugate outer diameter of the connecting portion.

18. The occluding device of claim 16, wherein the device is configured to be received within a delivery device in the contracted state for delivery to a target site within a patient's body, and wherein the device is configured to self expand to the expanded state when the device is deployed from the delivery device proximate the target site.

19. The occluding device of claim 16, wherein, in the expanded state, the distal portion defines a central part and first and second outer parts disposed at opposite ends of the major axis, the central part defines a plane, and each of the first and second outer parts extends out of the plane.

20. The occluding device of claim 19, wherein the first and second outer parts extend distally.

21. The occluding device of claim 19, wherein each of the first and second outer parts comprises a bend.

22. The occluding device of claim 19, wherein each of the first and second outer parts comprises a curve.

23. The occluding device of claim 16, wherein the proximal portion, the connecting portion, and the distal portion are coaxial with each other.

24. The occluding device of claim 16, wherein one of the proximal portion or the distal portion is coaxial with the connecting portion.

25. The occluding device of claim 16 further comprising an inner layer and an outer layer, wherein the inner and outer layers define at least one of the proximal portion, the connecting portion, or the distal portion.

26. The occluding device of claim 25, wherein the inner and outer layers define at least the connecting portion, and wherein the inner layer defines a waist within the connecting portion having a diameter that is smaller than an outer diameter defined by the outer layer in the connecting portion.

27. The occluding device of claim 25 further comprising a proximal end feature fixed to the proximal portion of the occluding device and a distal end feature fixed to the distal end of the occluding device so as to couple the layers together.

28. The occluding device of claim 27, wherein at least one of the proximal or distal end features is configured to releasably attach the occluding device to a delivery device.

29. The occluding device of claim 28, wherein at least one of the proximal or distal end features comprises an alignment feature that is configured to engage a corresponding alignment feature of the delivery device to limit rotation of the occluding device with respect to the delivery device.

30. The occluding device of claim 25 further comprising a supplementary layer associated with at least one of the proximal portion, the distal portion, or the connecting portion.

31. The occluding device of claim 30, wherein the inner layer defines a waist in the connecting portion, wherein the supplementary layer is substantially circular and defines a slit and a circumferential fold, and wherein the slit is configured to engage the inner layer proximate the waist such that a folded edge of the supplementary layer approximates a cylindrical configuration of the outer layer in the connecting portion.

32. A device for treating a target site comprising:
an outer layer; and
an inner layer disposed within the outer layer,
wherein, the inner and outer layers define:
a proximal portion that is substantially circular when viewed from a proximal end of the device,
a distal portion coaxial with the proximal portion, wherein the distal portion is substantially ovaloid when viewed from a distal end of the device, and
a connecting portion extending between the proximal portion and the distal portion and coaxial with the proximal and distal portions.

33. The device of claim 32, wherein the inner and outer layers are configured to be constrained in a contracted state and to assume an expanded state when unconstrained.

34. The device of claim 33, wherein the target site is a septal defect, and wherein the device is configured to be received within a delivery device in the contracted state and is configured to self expand to the expanded state when deployed from the delivery device such that each of the proximal portion and the distal portion engages a corresponding septal wall surface and the connecting portion is disposed within the septal wall.

35. The device of claim 32, wherein, in the expanded state, the proximal portion defines a proximal outer diameter, the distal portion defines a transverse outer diameter along a major axis of the ovaloid and a conjugate outer diameter along a minor axis of the ovaloid, and the connecting portion defines an outer diameter, and wherein the outer diameter of the connecting portion is smaller than the proximal outer diameter and the conjugate outer diameter.

36. The device of claim 32, wherein, in the expanded state, the distal portion defines a central part and first and second outer parts disposed at opposite ends of a major axis of the ovaloid, the central part defines a plane, and each of the first and second outer parts extends distally out of the plane.

37. The device of claim 36, wherein each of the first and second outer parts comprises a bend.

38. The device of claim 36, wherein each of the first and second outer parts comprises a curve.

39. The device of claim 32 further comprising a supplementary layer associated with at least one of the proximal portion, the distal portion, or the connecting portion, and wherein the supplementary layer includes a polymeric material.

40. A device for occluding a septal defect, wherein the device is configured to be constrained in a contracted state and to assume an expanded state when unconstrained, the occluding device comprising:
an outer layer; and
an inner layer disposed within the outer layer,
wherein, the inner and outer layers define:
a proximal portion that is substantially circular when viewed from a proximal end of the device,
a distal portion, wherein the distal portion is substantially ovaloid when viewed from a distal end of the device, and
a connecting portion extending between the proximal portion and the distal portion,
wherein the distal portion defines a central part and first and second outer parts extending from the central part, wherein the central part defines a plane, and wherein each of the first and second outer parts extends distally out of the plane,
wherein the occluding device is configured to be received within a delivery device in a contracted state and is configured to self expand to the expanded state when deployed from the delivery device such that each of the proximal portion and the distal portion engages a corresponding septal wall surface and the connecting portion is disposed within the septal wall.

41. The occluding device of claim 40, wherein the inner layer defines a waist within the connecting portion having a diameter that is smaller than an outer diameter defined by the outer layer in the connecting portion.

* * * * *